United States Patent [19]
Tenner et al.

[11] Patent Number: 5,965,439
[45] Date of Patent: Oct. 12, 1999

[54] HOST DEFENSE ENHANCEMENT

[75] Inventors: Andrea J. Tenner; Ronald R. Nepomuceno, both of Irvine, Calif.

[73] Assignee: The Regents of the University of California, Oakland, Calif.

[21] Appl. No.: 08/751,305

[22] Filed: Nov. 18, 1996

[51] Int. Cl.$^6$ .............................. C12N 15/00; C12N 5/00; C07H 21/04
[52] U.S. Cl. ....................... 435/455; 435/320.1; 435/325; 435/440; 536/23.5
[58] Field of Search ........................... 514/44; 435/172.3, 435/320.1, 325, 440, 455; 536/23.1, 23.5; 530/350; 424/93.1, 93.21

[56] References Cited

U.S. PATENT DOCUMENTS

| | | | |
|---|---|---|---|
| 4,946,788 | 8/1990 | Delespesse | 435/240.27 |
| 5,552,282 | 9/1996 | Caskey et al. | 435/6 |

FOREIGN PATENT DOCUMENTS

WO 93/18047   9/1993   WIPO.

OTHER PUBLICATIONS

Tenner et al., "Mannose binding protein (MBP) enhances mononuclear phagocyte function via a receptor that contains the 126,000 Mr component of the C1q receptor", *Immunity*, vol. 3, No. 4, Oct. 1995, pp. 485–493.

Crockard et al., "Increased expression of C1q receptors on neutrophils from inflammatory joint fluids", *Immunology Letters*, vol. 36, 1993, pp. 195–202.

Ghebrehiwet et al., "Isolation, cDNA cloning and overexpression of a 33–kD cell surface glycoprotein that binds to the globular "heads" of C1qa", *The Journal of Expreimental Medicine*, vol. 179, No. 6, Jun. 1, 1994, pp. 1809–182

Nepomuceno et al., "cDNA cloning and primary structure analysis of C1qRp, the human C1q/MBL/SPA receptor that mediates enhanced phagocytosis in vitro", *Immunity*, vol. 6, No. 2, Feb. 1997, pp. 119–129.

Crystal, R. G. Transfer of genes to humans: early lessons and obstacles to success. Science, vol. 270, pp. 404–410, Oct. 20, 1995.

Orkin et al. Report and recommendations of the panel to assess the NIH investment in research on gene therapy. Distrubuted by the National Institutes of Health, Bethesda, MD, Dec. 7, 1995.

Turner, "Mannose–binding lectin: the pluripotent molecule of the innate immune system", *Immunology Today*, vol. 17, No. 11, pp. 532–540, (1996).

Randi, "Itatel Group: Italian telecom for the next century", *Scientific American*, 262:40, (1990).

Jaenisch, "Germ line integration and Mendelian transmission of the exogenous Moloney leukemia virus", *Proc. Nat. Acad. Sci. USA*, vol 73, No. 4, pp. 1260–1264, (1976).

Furth et al., "Temporal control of gene expression in transgenic mice by a tetracycline–responsive promoter", *Proc. Natl. Acad. Sci. USA*, 91:9302–9306, (1994).

Li et al., "Targeted Mutation of the DNA Methyltransferase Gene Results in Embryonic Lethality", *Cell*, 69:915–926, (1992).

Stewart et al., "Expression of retroviral vectors in transgenic mice obtained by embryo infection", *EMBO Jrnl*, Vo. 6, No. 2, pp. 383–388, (1987).

Rosenberg et al., "Vectors for selective expression of cloned DNAs by T7 RNA polymerase", *Gene*, 56:125–135, (1987).

Gossler et al., "Transgenesis by means of blastocyst–derived embryonic stem cell lines", *Proc. Natl. Acad. Sci. USA*, 33:9065–9069, (1986).

Cheng et al. "Nonsense Condons Can Reduce the Abundance of Nuclear mRNA without Affecting the Abundance of Pre–mRNA or the Half–Life of Cytoplasmic mRNA", *Mol. and Cell Biol.*, vol. 13, No. 3, pp. 1892–1902, (1993).

Hanson et al., "Analysis of Biological Selections for High Efficiency Gene Targeting", *Mol. and Cell Biol.*, vol. 15, No. 1, pp. 45–51 (1995).

Deng et al., "Reexamination of Gene Targeting Frequency as a Function of the Extent of Homology between the Targeting Vector and the Target Locus", *Mol. and Cell Biol.*, Vo. 12, No. 8, pp. 3365–3371 (1992).

Urlaub et al., "Nonsense Mutations in the Dihydrofolate Reductase Gene Affect RNA Processing", *Mol. and Cell Biol.*, vol. 9, No. 7, (1989).

Daar, et al. "Premature Translation Termination Mediates Triosephosphate Isomerase mRNA Degradation", *Mol. and Cell Biol.*, vol. 8, No. 2, pp. 802–813, (1988).

Wolff et al., "Direct Gene Transfer into Mouse Muscle in Vivo", *Science*, 247:1465, (1990).

Wang et al., "Mice lacking ornithine–δ–amino transferase have paradoxical neonatal hypoornithinaemia and retinal degeneration", *Nature Genetics*, 11:185, (1995).

Andrikopoulos, et al., "Targeted mutation in the col5a2 gene reveals regulatory role for type V collagen during matrix assembly", *Nature Genetics*, 9:31–36, (1995).

Bradley et al., "Formation of germ–line chimaeras from embryo–derived teratocarcinoma cell lines", *Nature*, 309:255–256, (1984).

Evans et al., "Establishment in culture of pluripotential cells from mouse embryos", *Nature*, 292:154–156, (1981).

Jähner et al., "De novo methylation and expression of retroviral genomes during mouse embryogenesis", *Nature* 298:623–626, (1982).

(List continued on next page.)

*Primary Examiner*—Brian R. Stanton
*Assistant Examiner*—Deborah J. R. Clark
*Attorney, Agent, or Firm*—Fish & Richardson P.C.

[57]   ABSTRACT

Nucleic and amino acid sequences for a novel cell surface transmembrane glycoprotein designated ClqR$_P$ are taught. A method by which the nucleic acid sequence encoding ClqR$_P$ may be used to modulate the role of the immune system is also described. Transgenic animals created with heterologous DNA sequence encoding ClqR$_P$ are described as well as antibodies directed against the ClqR$_P$ protein. A method of hybridization for ClqR$_P$ nucleic acid using oligonucleotide probes based on the ClqR$_P$ nucleic acid sequence and methods for detecting a hybrid probe:target ClqR$_P$ duplex are also taught including a kit for such detection.

10 Claims, 6 Drawing Sheets

OTHER PUBLICATIONS

Köhler et al., "Continuous cultures of fused cells secreting antibody of predefined specificity", Nature 256:495–497 (1975).

Ono et al., "Plasmid DNAs directly injected into mouse brain with lipofectin can be incorporated and expressed by brain cells", Neuroscience Letters, 117:259–263, (1990).

Wu et al., "Receptor–mediated Gene Delivery and Expression in Vivo", Jrnl. Biol. Chem., vol. 263, No. 29, pp. 14621–14624, (1988).

Lee et al., "Proliferin Secreted by Cultured Cells Binds to Mannose 6–Phosphate Receptors", Jrnl. Biol. Chem., vol. 263, No. 7, pp. 3521–3527, (1988).

Fraley et al., "New generation liposomes: the engineering of an efficient vehicle for intracellular delivery of nucleic acids", TIBS, pp. 77–80, (Mar. 1981).

Felgner et al., "Lipofection: A highly efficient, lipid–mediated DNA–transfection procedure", Proc. Natl. Acad. Sci. USA, 84:7413–747, (1987).

Marcus–Sekura, "Techniques for Using Antisense Oligodeoxyribonucleotides to Study Gene Expression", Analytical Biochemstry, 172:289–295, (1988).

Straubinger et al., "Liposomes as Carriers for Intracellular Delivery of Nucleic Acids", Methods in Enzym. 101:512, (1983).

Cross et al., "Pretreatment with Recombinant Murine Tumor Necrosis Factor α/Cachetin and Murine Interleukin 1 α Protects Mice from Lethal Bacterial Infection", Jrnl. Exp. Med., 169:2021–2027, (1989).

Bohnsack et al., "Connective Tissue Proteins and Phagocytic Cell Function", Jrnl. Exp. Med., 161:912–923 (1985).

Argraves et al., "Amino Acid Sequence of the Human Fibronectin Receptor", Jrn. Cell Biol., 105:1183–1190, (1987).

Tenner et al., "Purification and Radiolabeling of Human $C1q^1$", Jrnl. Immunol., vol. 127, No. 2, pp. 648–653, (1981).

Gu et al., "Deletion of a DNA Polymerase β Gene Segment in T Cells Using Cell Type–Specific Gene Targeting", Science, 265:103–106 (1994).

Jaenisch, "Transgenic Animals", Science, 240:1468–1474, (1988).

Stothers, "Periodicity of the Earth's magnetic reversals", Nature, 322:444–446 (1986).

Ezekowitz, et al., "Molecular Characterization of the Human Macrophage Mannose Receptor: Demonstration of Multiple Carbohydrate Recognition–like Domains and Phagocytosis of Yeasts in COS–1 Cells", J. Exp. Med., 172:1785–1794, (1990).

Brinster et al., "Factors affecting the efficiency of introducing foreign DNA into mice by microinjecting eggs", Proc. Natl. Acad. Sci. USA., 82:4438–4442 (1985).

Jähner et al., "Insertion of the bacterial gpt gene into the germ line of mice by retroviral infection", Proc. Natl. Acad. Sci. USA, 82:6927–6931 (1985).

van der Putten et al., "Efficient insertion of genes into the mouse germ line via retroviral vectors", Proc. Natl. Acad. Sci. USA, 82:6148–6152 (1985).

Lammli, "Cleavage of Structural Proteins during the Assembly of the Head of Bacteriophage T4", Nature, 227:680–685 (1970).

Sauer et al., "Site–specific DNA recombination in mammalian cells by the Cre recombinase of bacteriophage P1", Proc. Natl. Acad. Sci. USA, 85:5166–5170 (1988).

Towbin et al., "Electrophoretic transfer of proteins from polyacrylamide gels to nitrocellulose sheets: Procedure and some applications", Proc. Natl. Acad. Sci. USA, 76:4350–4345 (1979).

Bobak et al., "C1q acts synergistically with phorbol dibutyrate to activate CR1–mediated phagocytosis by human mononuclear phagocytes", Eur. J. Immunol. 18:2001–2007 (1988).

Stacey et al., "Use of Double–Replacement Gene Targeting To Replace the Murine α–Lactalbumin Gene with Its Human Counterpart in Embryonic Stem Cells and Mice", Mol. and Cell Biol., vol. 14, No. 2, pp. 1009–1016 (1994).

Kühn, et al., "Inducible Gene Targeting in Mice", Science 269:1427–1429 (1995).

Bobak et al., "Characterization of C1q Receptor Expression on Human Phagocytic Cells: Effects of PDBu and fMLP", J. Immunol., vol. 136, No. 12, pp. 4604–4610 (1986).

Lowrance et al., "Spontaneous Elaboration of Transforming Growth Factor β Suppresses Host Defense against Bacterial Infection in Autoimmune MRL/lpr Mice", J. Exp. Med., 180:1693–1703 (1994).

Guan et al., "Cell–Surface Protein Identified on Phagocytic Cells Modulates the C1q–Mediated Enhancement of Phagocytosis", J. Immunol., 152:4005 (1994).

Young et al., "Complement Subcomponent C1q Stimulates Ig Production By Human B Lymphocytes", J. Immunol., 146:3356–3364, (1991).

Wu et al., "Targeting Genes: Delivery and Persistent Expression of a Foreign Gene Driven by Mammalian Regulatory Elements in Vivo", J. Biol. Chem., vol. 264, No. 29, pp. 16985–16987 (1989).

Testerman et al., "Cytokine induction by the immunomodulators imiquimod and S–27609", J. Leuk. Biol., 58:365–372 (1995).

Brigham et al., "Rapid Communication: In Vivo Transfection of Murine Lungs with a Functioning Prokaryotic Gene Using a Liposome Vehicle", Amer. Jrnl. Med. Sci., vol. 298, No. 4, pp. 278–281 (1989).

Craig et al., Modern Pharmacology, 2d ed., pp. 127–133, (1986).

Speight, Avery's Drug Treatment: Principles and Practice of Clinical Pharmacology and Therapeutics, 3d ed., pp. 50–56, (1987).

Spilker, Guide to Clinical Studies and Developing Protocols, Raven Press Books, Ltd., pp. 54–60 (1984).

Tallarida et al., Principles in General Pharmacology, Springer–Verlag, pp. 18–20, (1988).

Drickamer, "Two Distinct Classes of Carbonydrate–recognition Domains in Animal Lectins", J. Biol. Chem., vol. 263, No. 20, pp. 9557–0560, (1988).

Drickamer et al., "Mannose–binding Proteins Isolate from Rat Liver Contain Carbohydrate–recognition Domains Linked to Collagenous Tails", J. Biol. Chem., vol. 261, No. 15, pp. 6878–6887 (1986).

Patschinsky et al., "Analysis of the sequence of amino acids surrounding sites of tyrosing phosphorylation", Proc. Natl. Acad. Sci. USA, 79:973–977 (1982).

Lionetti et al., Methods of Cell Separation, Plenum Publ. Corp., p. 141 (1980).

Spilker, Guide to Clinical Studies and Developing Protocols, Raven Press Books, Ltd., pp. 7–14 (1984).

Ward et al., "Strategies for internal amino acid sequence analysis of proteins separated by polyacrylamide gel electrophoresis", J. Chrom., 519:199–216 (1990).

Rees et al., "The role of β–hydroxyaspartate and adjacent carboxylate residues in the first EGF domain of human factor IX", *EMBO Jrnl.,* vol. 7, No. 7, pp. 2053–2061 (1988).

Hobbs, et al., "Patterns of Cytokine Gene Expression by $CD4^+$ T Cells from Young and Old Mice", *J. Immunol.,* 150:3602–3614 (1993).

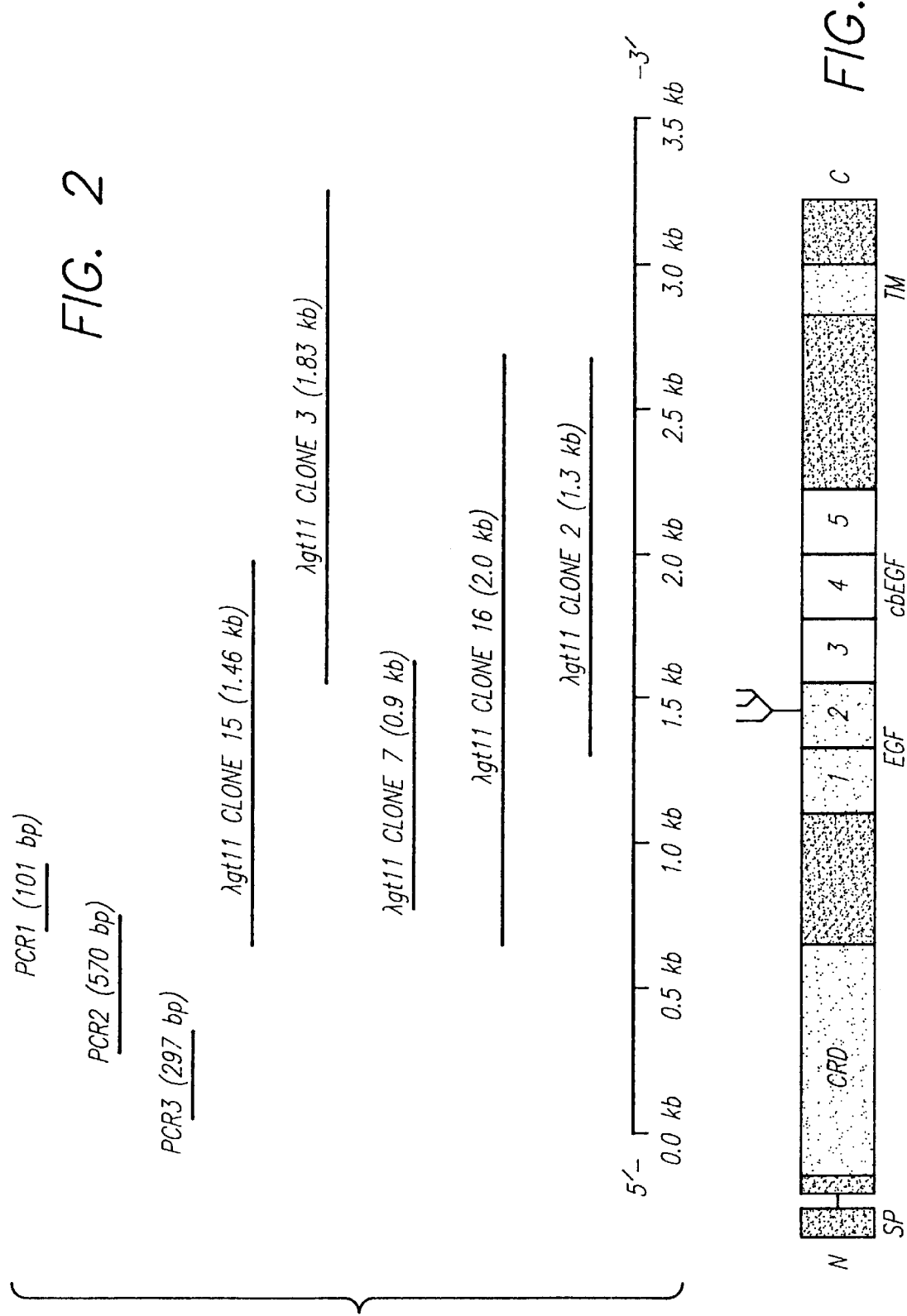

FIG. 3-A

```
-147  AAGCCCTCAGCCTTTGTGTCCTTCTCTGCGCCGAGTGGCTGCAGCTCACCCCTCAGCTCCCCCTTGGGCCCAGCTGGGAGCCGAGATAGAAGCTCCTG A   -148
 -48  TCGCCGCTGGGCTTCTCGCCTCTCCCGCAGAGGGCCACACAGAGACCGGGATGGCCACCTCCATGGGCCTGCTGCTGCTGCTGCTGCTCCTGACCCAG      -49
                                                          M  A  T  S  M  G  L  L  L  L  L  L  L  T  Q     51
                                                                                                           17
  52  CCCGGGGCGGGGACGGGAGCTGACACGGAGGCGGTGTCTGCGTGGGACCGCTGCGTCTACACGGCCCACTCGGGCAAGCTGAGCGCTGCCGAGGCCAG    150
  18  P  G  A  G  T  G  A  D  T  E  A  V  V  C  V  G  T  A  C  Y  T  A  H  S  G  K  L  S  A  A  E  A  Q     50

151  AACCACTGCAACCAGAACGGGGGCAACCTGGCCACTGTGAAGAGCAAGGAGGAGGCCCAGCACGTCCAGCGAGTACTGGCCCAGCTCCTGAGGCGGGAG    249
  51  N  H  C  N  Q  N  G  G  N  L  A  T  V  K  S  K  E  E  A  Q  H  V  Q  R  V  L  A  Q  L  L  R  R  E     83

250  GCAGCCCTGACGGCGGAGGATGAGCAAGTTCTGGATTGGGCTCCAGGGACCTAGTGCCTGGACCCTAGTGCTGCGCTGAAGGGCTTCAGCTGG       348
  84  A  A  L  T  A  R  M  S  K  F  W  I  G  L  Q  R  E  K  G  K  C  L  D  P  S  L  P  L  K  G  F  S  W    116

349  GTGGGCGGGGAGGACACGCCTTACTCTAACTGGCACAAGGAGCTCCGGAACTCTGTGCATCTCCAAGCGCTGTGTCTCTGTGGACCTGTCC          447
 117  V  G  G  E  D  T  P  Y  S  N  W  H  K  E  L  R  N  S  C  I  S  K  R  C  V  S  L  L  L  D  L  S      149

448  CAGCCGCTCCTTCCCAACCGCCTGCCCAAGTGGTCTGAGGGCCCAAGTGGTCTGAGGGCCCCTGTGGGAGCCCAGGCTCCCCGGAAGTAACATTGAGGGCTTCGTGTGCAAGTTC 546
 150  Q  P  L  L  P  N  R  L  P  K  W  S  E  G  P  C  G  S  P  G  S  N  I  E  G  F  V  C  K  F          182

547  AGCTTCAAAGGCATGTGCCGCCCACTGGCCCTGGGGCCCGGGGCCCTGGGGCCCGGGGAGGTGACCTACACCACCCCCTTCCAGACCACCAGTTCCTCCTTGGAGGCTGTG 645
 183  S  F  K  G  M  C  R  P  L  A  L  G  G  P  G  Q  V  T  Y  T  T  P  F  Q  T  T  S  S  L  E  A  V    215

646  CCCTTTGCCTCTGCGGCCAATGTAGCCTGTGTGGGAGAAGGTGACAAGGACGAGACTCAGAGTCATTATTTCCTGTGCAAGGAGAAGGCCCCCGATGTGTTC 744
 216  P  F  A  S  A  A  N  V  A  C  G  E  G  D  K  D  E  T  Q  S  H  Y  F  L  C  K  E  K  A  P  D  V  F    248

745  GACTGGGCAGCTCGGGCTCCCCTCTGTCAGCCCAAGTATGGCTGCAACTTCAACAATGGGGGCTGCCACCAGGACTGCTTTGAAGGGGGGATGGC      843
 249  D  W  G  S  S  G  P  L  C  V  S  P  K  Y  G  C  N  F  N  N  G  G  C  H  Q  D  C  F  E  G  G  D  G   281
```

FIG. 3-B

```
 844  TCCTTCCTCTGCGGCTGCCGACCAGGATTCCGGCTGCTGGATGACCTGGTGACCTGTGCCTCTCGAAACCCTTGCAGTCCAGCCCATGTCGTGGGGGG   942
 282   S  F  L  C  G  C  R  P  G  F  R  L  L  D  D  L  V  T  C  A  S  R  N  P  C  S  S  S  P  C  R  G  G   314

943  GCCACGTGCGTCCTGGGACCCCATGGGAAAAACTACACGTGCCGCTGCCCCCAAGGGTACCAGCTGGACTCGAGTCAGTCAGCTGGATCAGTGTGGACGTGGAT  1041
 315   A  T  C  V  L  G  P  H  G  K  N  Y  T  C  R  C  P  Q  G  Y  Q  L  D  S  S  Q  L  D  C  V  D  V  D   347

1042  GAATGCCAGGACTCCCCTGTGCCCAGGAGTGTGTCAACACCCCTGGGGGCTTCCGCTGCGAATGTGGGTTGGCTATGAGCCGGGCGGTCCTGGAGAG  1140
 348   E  C  Q  D  S  P  C  A  Q  E  C  V  N  T  P  G  G  F  R  C  E  C  W  V  G  Y  E  P  G  G  P  G  E   380

1141  GGGGCCTGTCAGGATGTGGATGAGTGTGCTCTGGGTCGCTCGCCTTGCGCCCAGGGCTGCACCAACACAGATGGCTCATTTCACTGCTCCTGTGAGGAG  1239
 381   G  A  C  Q  D  V  D  E  C  A  L  G  R  S  P  C  A  Q  G  C  T  N  T  D  G  S  F  H  C  S  C  E  E   413

1240  GGCTACGTCCTGGCCGGGGAGGACGGACTCAGTGCCAGGAGACGTGGATGAGTGTGTGGGCCCCCTCTGCGACAGCTTGTGCTTCAACACA  1338
 414   G  Y  V  L  A  G  E  D  G  T  Q  C  Q  D  V  D  E  C  V  G  P  G  G  P  L  C  D  S  L  C  F  N  T   446

1339  CAAGGGTCCTTCCACTGTGGCTGCCTGCCAGGCTGGGTGCTGGCCCCAAATGGGGTCTCTTGCACCATGGGACCCGTGTCTCTGGGACCACCATCTGGG  1437
 447   Q  G  S  F  H  C  G  C  L  P  G  W  V  L  A  P  N  G  V  S  C  T  M  G  P  V  S  L  G  P  P  S  G   479

1438  CCCCCCGATGAGGAGGACAAAGGAGAGAAGGAGGCACCGTGCCCCGAGGGCACCCCAAGGCT  1536
 480   P  P  D  E  E  D  K  G  E  K  E  G  S  T  V  P  R  A  A  T  A  S  P  T  R  G  P  E  G  T  P  K  A   512

1537  ACACCCCACCACAAGTAGACCTTCGCTGTCATCTGACGCCCCATCACATCTGCCCACTCAAGATGCTGGCCCCAGTGGTCCTCAGGCGTCTGGAGG  1635
 513   T  P  T  T  S  R  P  S  L  S  S  D  A  P  I  T  S  A  P  L  K  M  L  A  P  S  G  S  S  G  V  W  R   545

1636  GAGCCCAGCATCCATCACGCCACAGCTGCCTCTGCCCCAGGAGCTGCAGGTGGGGACTGGGGGAGGGGACTCGTGGCCACACAAAACAACGATGGCACTGACGGG  1734
 546   E  P  S  I  H  H  A  T  A  A  S  G  P  Q  E  P  A  G  G  D  S  S  V  A  T  Q  N  N  D  G  T  D  G   578
```

FIG. 3-C

```
1735 CAAAAGCTGCTTTTATTCTACATCCTAGGCACCGTGGTGGCCATCCTACTCCTGCTGGGCTACTGGTCTCGCAAGCGGAGAGCG   1833
579   Q  K  L  L  L  F  Y  I  L  G  T  V  V  A  I  L  L  L  L  G  Y  W  S  R  K  R  R  A      611

1843 AAGAGGGAGGAGAAGAAGGAGAAGAAGCCCCAGAATGCGGCAGACAGTTACTCCTGGGTTCCAGAGCGAGCTGAGAGACCAGTAC   1932
612   K  R  E  E  K  K  E  K  K  P  Q  N  A  A  D  S  Y  S  W  V  P  E  R  A  E  S  R  A  M  E  N  Q  Y   644

1933 AGTCCGACACCTGGGACAGACTGCTGAAAGTGAGGTGGCCCTAGAGACACTAGAGTCACCAGCCACCATCCTCAGAGCTTTGAACTCCCCATTCCAAAG   2031
645   S  P  T  P  G  T  D  C  *                                                                            652

2032 GGGCACCCACATTTTTTGAAAGACTGGAATCTTAGCAAACAATTGTAAGTCTCCTCCTTGGAACATGCAGGTATTTTCTACG   2130
2131 GGTGTTTGATGTTTCCTGAAGTGGAAGCTGTGTGTTGGCGTGCTGCCACGGTGGGGATTTCGTGCTGTTACTCCCCTCCCTTTCAAATT   2229
2230 CCAATGTGACCAATTCCGGATCAGGGTGTGAGGAGGCTAGGGGCTCCCTAGGATGAAAACTAAATCAATTATTCAATTAGGTAAGAGAATCTGGTT   2328
2329 TGAGTGTGCTCATGCTGATTAGGATTGAAATGATTTGTTTCTCTTCCTAGGATGAAAACTAAATCAATTATTCAATTAGGTAAGAGAATCTGGTT   2427
2428 TTTGGTCAAAGGGAACATGTTCGGACTGGAAACATTCTTTACATTTGCATTCCTGCCAGCACAGTCTTGCTAAATGTGATACTGTTGACA   2526
2527 TCCTCCAGAATGGCCAGAAGTGCAATTAACCTCTTAGGTGGCAAGGAGGCAGGAAGTGCCTCTTTAGTTCTTACATTTCTAATAGCCTTGGGTTATT   2625
2626 GCAAAGGAAGCTTGAAAAATATGAATTAATTGAGAAAAGTTGCTTGAAGTGCATTACAGGTGTTTGTGAAGTCACATAATCTACGGGCTAGGGCGAGAGAGGCCAGG   2724
2725 GATTTGTTCACAGATACTTGAGCCAGGGCAGGCTCAGGCAGGCTCCATCAGGCTGTTTCCAAATGTACTGAGGTTGATCAACAAGGAAACAAATTCA   2823
2824 AGGACAACCTGTCTCTTTGAGCCAGAAAGTTCCATCAGGCAGGCTCCATCAGGCTGTTTCCAAATGTACTGAGGTTGATCAACAAGGAAACAAATTCA   2922
2923 CAGAGGAAGCCCTGCAGAAAGTTCATCAGGCAGCATCCGAGATTTTAAATCCTGAAGTGTGGCGCACACACCAAGTAGGGAGCTAGTCAGGCAG   3021
3022 TTTAGCACAGTTCATGTCCACAGTTGATGCAGCATCCTGAGATTTTAAATCCTGAAGTGTGGCGCACACACCAAGTAGGGAGCTAGTCAGGCAT   3120
3121 TTTGCTTAAGGAACTTTTGTTCTCTGTCTCTCTTTTTCCTTAAAATTGGGGGTAAGGAGGTAAGGAGGTAAGAAGTTACATTTGCAAATATTTCTCCCATGATAATCATTTTTAC   3219
3220 AGCAAAAACTGCTCAAGCCATTTAAATTATATCCTCATTTTAAAAGTTACATTTGCAAATATTTCTCCCTATGATAATGCAGTCAGTAGTGT   3312
```

HOST DEFENSE ENHANCEMENT

The present invention was made with Government support by the National Institutes of Health/National Cancer Institute Training Program in Carcinogenesis (5T32-C-A09054) and National Institutes of Health Grant # AI-41090. The government has certain rights associated with the invention.

BACKGROUND OF THE INVENTION

1. Field of the Invention

This invention relates generally to compositions, and methods of employing these compositions for the enhancement of host defense. More specifically, it relates to the use of various forms of the human $ClqR_P$ receptor, their use in enhancing host defense, methods of detection, methods of hybridization and methods of determining novel homologous $ClqR_P$ receptors and ligands and transgenic animals thereof.

2. Description of Related Art

The following is a general description of art relevant to the present invention. None is admitted to be prior art to the invention. Generally, this art relates to observations of the complement receptors of the immune system.

INTRODUCTION

Phagocytosis is a major host defense mechanism by which potentially deleterious material (both pathogenic organisms and cellular debris) is cleared from circulation and tissue, and made accessible to inactivation. The phagocytic capacity/potential of a cell can be modulated by cytokines which trigger cellular differentiation or by other activation ligands. This activation is probably relevant at sites of inflammation where Clq and/or other regulatory molecules may accumulate and enhance the phagocytic capacity of acute inflammatory cells.

The complement component protein designated Clq, is part of a family of host defense proteins with similar macromolecular structures which include a collagen-like region contiguous with a globular domain. Clq is composed of covalently linked subunits of three distinct polypeptide chains each with N-terminal collagen-like regions: Clq is the recognition subunit of the Cl component of the classical complement pathway (CCP) in that it binds to the Fc region of antibodies in immune complexes, as well as a variety of non-immunoglobulin substances, and can initiate the classical complement pathway of the immune system.

Clq can enhance both FcR- and CRl-mediated phagocytosis by human monocytes. Specifically, the collagen-like fragment of Clq (Clq-CLF) is the region of the Clq molecule that mediates enhanced phagocytosis, since the phagocytic response can be triggered by the pepsin-resistant fragment only, and not by the pepsin-sensitive, collagenase-resistant fragments.

Enhancement of phagocytosis triggered by the Clq protein can be inhibited by monoclonal antibodies R139 and R3, indicating that the antigenic region of the Clq receptor protein which is recognized by these antibodies is a critical, functional component of the Clq receptor protein. These antibodies (R139 and R3) bind to a 126,000 $M_r$ (reduced) glycoprotein which is highly expressed on the surfaces of phagocytic cells, but not on B or T lymphoblastoid cells. Since these antibodies first described the Clq receptor that modulates monocyte phagocytosis, the protein (126,000 $M_r$) is designated $ClqR_P$. The antibodies that recognize $ClqR_P$ (R139 and R3) are also able to inhibit a myeloid cell response (enhanced monocyte phagocytosis), indicating a functional role for the $ClqR_P$ protein in myeloid cell types.

SUMMARY OF THE INVENTION

The invention provides Clq receptor ($ClqR_P$) sequences and nucleic acid sequences which encode for the novel cell surface transmembrane glycoprotein receptor designated $ClqR_P$. This receptor plays a role in stimulating the classic complement component of the immune system, specifically in stimulating phagocytosis in cells without a concomitant increase in inflammation. A method of hybridization based on the $ClqR_P$ nucleic acid sequence is provided as well as methods for detecting novel ligands for the $ClqR_P$, including those which function as agonists or antagonists. Additionally, methods of determining compositions which effect the formation of an affinity complex between the $ClqR_P$ and its ligand are provided as well as methods for determining compositions which modulate signal transduction via the $ClqR_P$. The nucleic acid sequence encoding $ClqR_P$ or recombinant $ClqR_P$ protein may be used to effect the role of this classical complement component of the immune system. Transgenic animals can be created using $ClqR_P$ DNA sequences to aid in the study of the role of $ClqR_P$ during growth and metabolism and as a model for disease states in which the normal level of $ClqR_P$ is effected.

The invention provides substantially pure $ClqR_P$ polypeptides, fragments thereof, nucleic acid sequences encoding $ClqR_P$ or fragments thereof, methods of detecting novel ligands of the $ClqR_P$, methods of administering formulations capable of gene delivery and gene expression of $ClqR_P$ nucleic acid, methods of hybridization for $ClqR_P$ nucleic acid, and transgenic animals created using $ClqR_P$ nucleic acid sequences.

The details of the preferred embodiment of the present invention are set forth in the accompanying drawings and the description below. Once the details of the invention are known, numerous additional innovations and changes will become obvious to one skilled in the art.

BRIEF DESCRIPTION OF THE DRAWINGS

FIG. 2. $ClqR_P$ PCR and λgt11 clones. Positions of the three PCR fragments and isolated λgt11 clones are shown. After the PCR1, PCR2 and clone 15 were sequenced, clones 2, 3, 7 and 16 were sequenced at the 5' and 3' ends to determine their positions. Clone 3 was then sequenced in its entirety. PCR3 was generated by the 5'-RACE PCR method.

FIG. 3. cDNA and deduced amino acid sequence of $ClqR_P$. (SEQ ID NO: 2) Nucleotides are numbered with the first base of the initiator methionine as +1. The amino terminus of the mature protein and internal peptides determined by amino acid sequencing are underlined. The single putative N-glycosylation site is in italics starting at position N325. The transmembrane domain is double underlined.

FIG. 4. Structural domains of $ClqR_P$. Shown is a schematic diagram indicating the domains contained within ClqR$_P$ which include a 21 amino acid signal peptide (SP) and a C-type carbohydrate recognition domain (CRD) at the N-terminus, five Epidermal Growth Factor (EGF)-like domains, numbered, including three calcium binding (cb) EGF domains, and a single transmembrane (TM) domain. The putative N-linked glycosylation site is indicated within the second EGF domain.

Like reference numbers and designations in the various drawings indicate like elements.

DETAILED DESCRIPTION OF THE INVENTION

Figure 1:
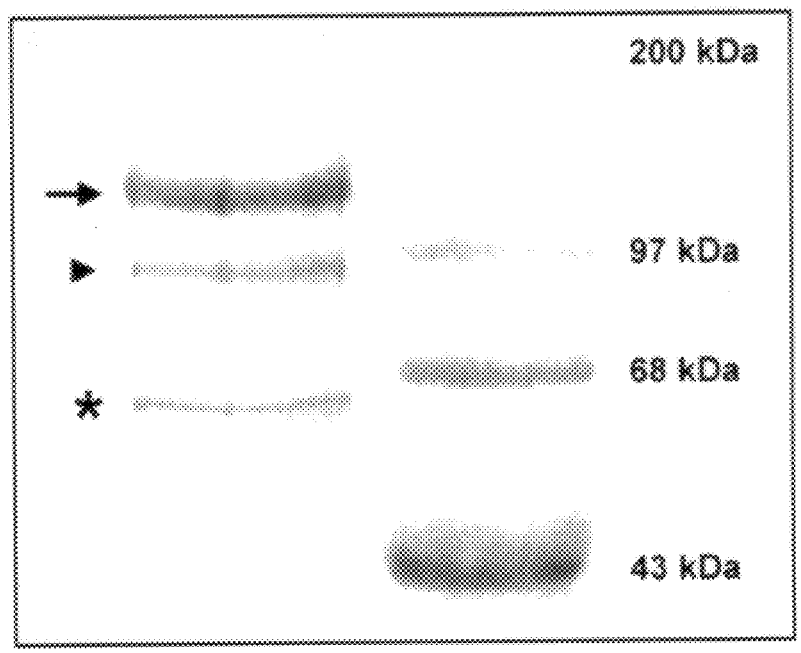
FIG. 1. Affinity purified $ClqR_P$. Immobilized purified monoclonal antibody R3 (IgM) was used to affinity purify the receptor antigen from detergent extracts of U937 cells. Eluted protein was concentrated and subjected to SDS-PAGE (7.5%) under reducing conditions followed by Coomassie Blue staining (left). Mature 126,000 $M_r$ $ClqR_P$ is indicated by the arrow. Breakdown fragments are indicated by the arrow-head and asterisk. Molecular weight markers are shown in the right lane.
Figure 5:
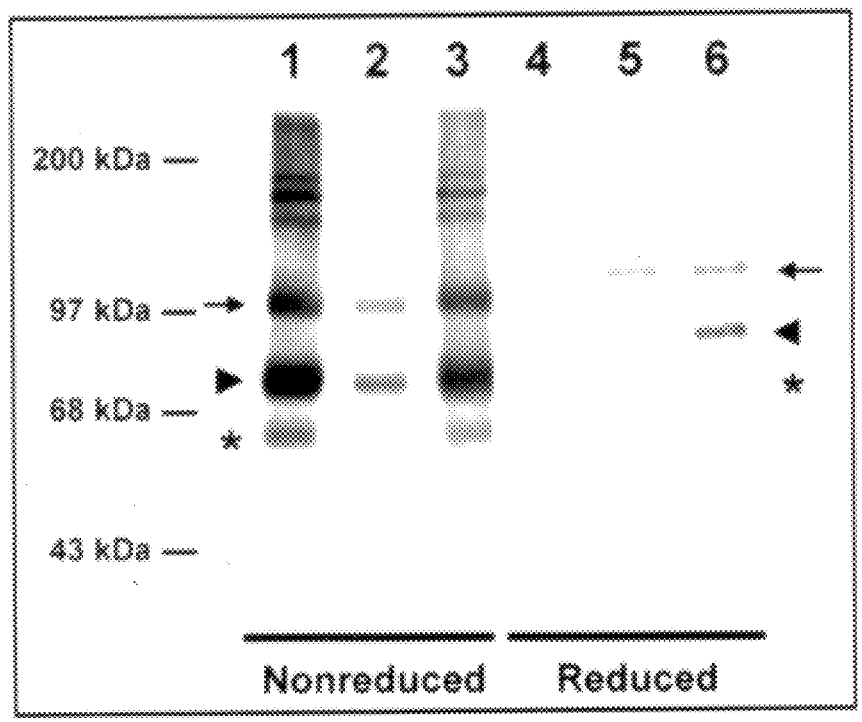
FIG. 5. Anti-peptide antibody recognizes ClqR$_P$. R3 purified ClqR$_P$ was subjected to SDS-PAGE under nonreducing (lanes 1–3) and reducing (lanes 4–6) conditions, then transferred to nitrocellulose. The blot was probed with monoclonal antibody R139 (lanes 1 and 4), polyclonal anti-peptide antiserum (lanes 2 and 5) and with polyclonal anti-ClqR$_P$ antiserum QR1 (lanes 3 and 6). Isotype and species matched antibodies were used as probes in parallel and resulted in no reactivity similar to lane 4 (not shown). Arrows indicate the intact receptor, whereas breakdown fragments are indicated by the arrowheads and asterisks. Molecular weights are indicated on the left.
Figure 6:
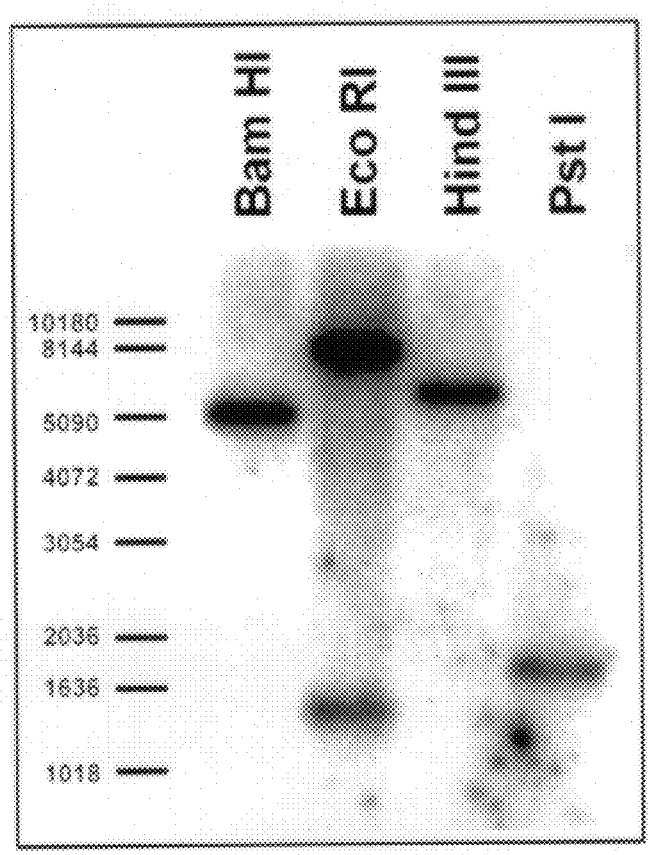
FIG. 6. Southern blot analysis of human genomic DNA for ClqR$_P$. DNA was digested with Bam HI, Eco R1, Hind III and Pst I. After agarose gel electrophoresis and transfer, the DNA was hybridized to a $^{32}$P-labeled probe generated by random priming of the λgt11 clone 15 insert. Positions of size markers (in base pairs) are indicated at the far left.
Figure 7:
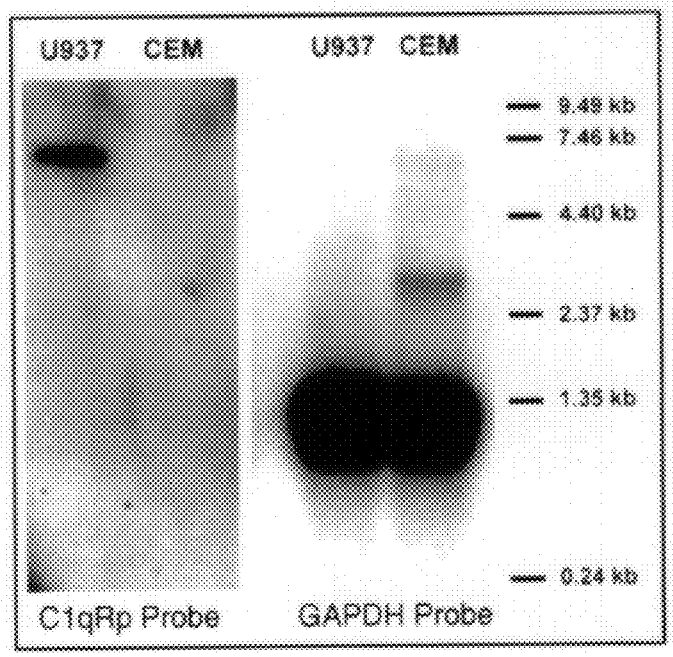
FIG. 7. Northern blot analysis of mRNA for ClqR$_P$. Messenger RNA was separated by agarose gel electrophoresis and transferred to nylon. The blot on the left was probed for ClqR$_P$ and the blot on the right was probed for GAPDH as a control for RNA levels. Positions of the 0.24–9.49 Kb RNA ladder are indicated on the far right.

Before the present nucleic and amino acid sequences, compositions, formulations and methods and uses thereof are described, it is to be understood that this invention is not limited to the particular compositions, formulations, sequences and methodologies described herein as such compositions, formulations, sequences and methodologies may vary. It is also to be understood that the terminology used herein is for the purpose of describing particular embodiments only, and that the terminology used herein is not intended to limit the scope of the present invention which will be limited only by the appended claims.

It must be noted that as used herein and in the appended claims, the singular forms "a," "an," and "the," include plural referents unless the context clearly indicates otherwise. Thus, for example, reference to "a formulation" includes one or more of such different formulations, reference to "an antibody" includes one or more of such different antibodies, and reference to "the method" includes reference to equivalent steps and methods known to those of ordinary skill in the art which could be modified or substituted for the methods described herein.

Unless defined otherwise, all technical and scientific terms used herein have the same meaning as commonly understood by one of ordinary skill in the art to which the invention belongs. Although any methods, compositions, formulations, sequences similar or equivalent to those described herein can be used in the practice or testing of the invention, the preferred methods and materials are described herein. All publications mentioned herein are incorporated herein, including all figures, graphs, equations, illustrations, and drawings, to describe and disclose specific information for which the reference was cited in connection with.

The publications discussed above are provided solely for their disclosure prior to the filing date of the present application. Nothing herein is to be construed as an admission that the invention is not entitled to antedate such disclosure by virtue of prior invention. Throughout this description, the preferred embodiment and examples shown should be considered as exemplars, rather than as limitations on the present invention.

The invention describes cDNA encoding the ClqR$_P$, the amino acid sequence encoding it, and functional domain structures of the ClqR$_P$ protein. The ClqR$_P$ protein plays a critical role in mediating cell signaling resulting in enhanced phagocytic capabilities of the signaled cell. The ClqR$_P$ protein contains the necessary molecular components needed to transduce a cell signal and it may play a critical role as a receptor of the immune system and in the complement branch of the immune system by functioning in the clearance of cells or cellular debris.

The ability to regulate the phagocytic capacity of myeloid cells via the regulation of cell surface expression and function of ClqR$_P$ will be valuable as a prophylactic treatment for individuals at risk for infection, such as individuals with genetic immunodeficiencies, or individuals infected with HIV, patients undergoing cancer chemotherapy, or patients undergoing high risk surgery.

Additionally, in vitro evidence indicates that ClqR$_P$ does not induce proinflammatory cytokines. This evidence suggests that monocyte activation of increased phagocytosis by employing the ClqR$_P$ sequences of the instant invention will be advantageous due to the selectivity of the ClqR$_P$ response and the ability of ClqR$_P$ not to induce an inflammatory reaction. Furthermore, ClqR$_P$ does not increase the levels of mRNA encoding for, or protein secretion of cytokines TNF-α, IL-1β or IL-6 which have been shown to increase inflammation.

The enhancement of the host immune system via activation of cells employing formulations encoding the ClqR$_P$ or employing formulations comprising recombinant ClqR$_P$ protein, as taught herein, may be more advantageous than employing pharmacologic agents which increase the risk of provoking proinflammatory cytokine release (Testerman et al., J. Leuk. Biol. 58 365, 1995). For example, the proinflammatory cytokine, Tumor Necrosis Factor alpha (TNFα), enhances the expression of the human immunodeficiency virus (HIV). Thus, initiating a cytokine response such as TNFα would be extremely undesirable when trying to enhance the microbicidal activity in a patient with a compromised immune system. The present invention overcomes such limitations by increasing host resistance to microbial invasion without creating an increased inflammatory response. Furthermore, the increase in the ClqR$_P$ phagocytosis response occurs rapidly, approximately within 5 minutes after interaction of a ClqR$_P$ expressing cell with the Clq protein or other ligand for Clq.

In addition to a lack of ClqR$_P$-mediated induction of proinflammatory cytokines, ClqR$_P$ substantially decreased existing elevated levels of the cytokines IL-1α, IL-1β, TNF-α and IL-6 mRNA levels and IL-1β, TNF-α and IL-6 protein secretion levels under certain conditions in vitro. Therefore, ClqR$_P$ mediated expression may be used prophylactically in treating immuno-compromised individuals and also as a means of effecting the levels of cytokines in a patient.

The invention provides substantially pure polynucleotides encoding the ClqR$_P$ protein or fragments thereof. These polynucleotides include DNA, cDNA and RNA sequences which encode $ClqR_P$. All polynucleotides encoding all or a portion of $ClqR_P$ are also included herein, as long as they encode a polypeptide with $ClqR_P$ activity or a functional fragment of a $ClqR_P$ molecule. $ClqR_P$ polypeptide fragments or portions thereof must comprise a segment of at least 5 consecutive amino acids that are conserved in any of $ClqR_P$ amino acid sequences listed herein. Such polynucleotides include naturally occurring, synthetic, and intentionally manipulated polynucleotides. For example, $ClqR_P$ polynucleotide may be subjected to site-directed mutagenesis. The polynucleotide sequence for $ClqR_P$ also includes antisense, nonsense, or missense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of $ClqR_P$ polypeptide or a part thereof encoded by the nucleotide sequence is functionally unchanged.

The invention also provides isolated nucleic acid molecules that encode the $ClqR_P$ polypeptides described above, as well as fragments thereof. These nucleic acids can contain naturally occurring nucleotide sequences (see FIG. 3), or sequences that differ from those of the naturally occurring nucleic acids that encode $ClqR_P$, but encode the same amino acids, due to the degeneracy of the genetic code. The nucleic acids of the invention can contain DNA or RNA nucleotides, or combinations or modifications thereof.

Definitions

By "isolated nucleic acid" is meant a nucleic acid, e.g, a DNA or RNA molecule, that is not immediately contiguous with the 5' and 3' flanking sequences with which it normally is immediately contiguous when present in the naturally occurring genome of the organism from which it is derived. The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

The nucleic acid molecules of the invention can be used as templates in standard methods for production of $ClqR_P$ gene products (e.g., $ClqR_P$ RNAs and $ClqR_P$ polypeptides; see below). In addition, the nucleic acid molecules that encode $ClqR_P$ polypeptides (e.g., SEQ ID NO:1 and fragments thereof) and related nucleic acids, such as (1) nucleic acids containing sequences that are complementary to, or that hybridize to, nucleic acids encoding $ClqR_P$ polypeptides, or fragments thereof (e.g., fragments containing at least 9, 12, 15, 20, or 25 nucleotides); and (2) nucleic acids containing sequences that hybridize to sequences that are complementary to nucleic acids encoding $ClqR_P$ polypeptides, or fragments thereof (e.g., fragments containing at least 9, 12, 15, 20, or 25 nucleotides); can be used in methods focused on their hybridization properties. For example, as is described in further detail below, such nucleic acid molecules can be used in the following methods: PCR methods for synthesizing $ClqR_P$ nucleic acids, methods for detecting the presence of $ClqR_P$ nucleic acid in a sample using oligonucleotide probes based on the $ClqR_P$ nucleic acid sequences supplied herein, which under stringent hybridization conditions will form $ClqR_P$ probe: $ClqR_P$ target duplexes without detectable formation of $ClqR_P$ probe:non-$ClqR_P$ target duplexes, and methods for detecting the hybrid $ClqR_P$ probe:$ClqR_P$ target duplex formed after successful hybridization of a $ClqR_P$ probe to its complementary target nucleic acid sequence can be supplied in a kit form, screening methods for identifying nucleic acids encoding new $ClqR_P$ family members or identifying test compounds or compositions which affect the binding to the $ClqR_P$ can also be supplied in a kit form, and therapeutic methods. The term sample, as used herein, comprises fluid, blood, serum, plasma, cells, tissue, swabs, or secretions or other clinical samples as are commonly familiar to those of ordinary skill in the clinical arts.

The term "kit" as used herein refers to any combination of elements or interrelated parts that are necessary for: detecting and determining the presence of $ClqR_P$ nucleic acid in a sample, screening for identifying nucleic acids encoding new $ClqR_P$ family members, or screening for identifying test compounds or compositions which affect binding to the $ClqR_P$. One skilled in the art would realize that although the physical characteristics of the kit or its contents are not characterized, those features necessary for the formation of a kit and its physical instantiation are supplied by the teachings of the disclosure herein, the attached claims, and the common knowledge concerning kits possessed by one of common skill in the art.

The term "substantially pure" is used herein to describe a molecule, such as a polypeptide (e.g., a $ClqR_P$ polypeptide, or a fragment thereof) that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. One skilled in the art can purify $ClqR_P$ polypeptides using standard protein purification methods and the purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

Also included in the invention are polypeptides having sequences that are "conservative variations" of the sequence of a $ClqR_P$ polypeptide. A "conservative variation" amino acid sequence is a sequence that differs from a reference sequence only by conservative amino acid substitutions, for example, substitutions of one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid, or glutamine for asparagine), or by one or more non-conservative substitutions, deletions, or insertions, provided that the polypeptide retains at least one $ClqR_P$-specific activity or a $ClqR_P$-specific epitope. For example, one or more amino acids can be deleted from a $ClqR_P$ polypeptide, resulting in modification of the structure of the polypeptide, without significantly altering its biological activity. For example, amino- or carboxyl-terminal amino acids that are not required for $ClqR_P$ biological activity, can be removed. Such modifications can result in the development of smaller active $ClqR_P$ polypeptides.

The term "$ClqR_P$" is used in accordance with its conventional definition. Such receptors are cell surface receptors that typically modulate monocyte phagocytosis by transducing signals from extracellular environments (e.g., the Clq protein) to intracellular environments. $ClqR_P$, is a novel cell surface transmembrane glycoprotein receptor that mediates an activation signal that results in an enhanced phagocytotic capacity of the ligated cell. Cell stimulation of the $ClqR_P$ is induced by the ligand protein Clq, or by a family of Clq-like proteins such as mannose binding lectin (MBL) or pulmonary surfactant protein A (SPA). The $ClqR_P$ glycoprotein is highly expressed on the surfaces of phagocytic cells, but not on B or T lymphoblastoid cells. This molecule has the necessary molecular components needed to transduce a signal and can be postulated to be a critical receptor of the innate immune system, as well as functioning in immune complex clearance and/or clearance of cellular debris. Antibodies to $ClqR_P$ (R3 and R139) inhibit Clq-, MBL-, and SPA-mediated, but not fibronectin-mediated, enhancement of phagocytosis. The $ClqR_P$ response does not trigger the release of proinflammatory cytokines in vitro suggesting that activation of the monocyte $ClqR_P$ by Clq and its other ligands is selective.

A "test composition", as used herein, is any composition such as a polypeptide, peptide fragment or composition created through the use of a combinatorial library or other combinatorial process that can be assayed for its ability to function in a given capacity (e.g, as a $ClqR_P$ ligand, or $ClqR_P$ antagonist or $ClqR_P$ agonist or modulator of signal transduction using the $ClqR_P$) or compound which mimics the activity of polypeptide (e.g., peptidomimetics). Often, such a test composition or polypeptide is, because of its sequence or structure, suspected of being able to function in a given capacity. Nonetheless, randomly chosen "test" polypeptides and compositions also can be used, and art-known techniques, such as expression of polypeptides from nucleic acid libraries, or PCR combinatorial generated polypeptides can be used to this end. A "ligand" is any composition (e.g., a polypeptide, polypeptpeptderivative, or peptidomimetic) that is capable of inducing signal transduction in a cell by contacting a $ClqR_P$. Included are compositions that naturally induce signal transduction via the $ClqR_P$; also included are compositions that do not naturally induce signal transduction (e.g., artificial compositions and natural compositions that serve other purposes). Compositions that merely bind a $ClqR_P$ without inducing signal transduction are not encompassed by the term ligand. The term "agonist" as used herein means any composition that is capable of increasing the ability of a ligand to bind a ClqR, or itself to bind to the ClqR, and induce signal transduction. Such an agonist need not bind the ligand to increase the ability of a ligand to bind the $ClqR_P$ or to modulate signal transduction via the $ClqR_P$. The term "antagonist" as used herein means any composition that is capable of decreasing the ability of a ligand to bind a $ClqR_P$ or to bind to the $ClqR_P$ itself to inhibit signal transduction via the $ClqR_P$ (e.g., by functioning as a competitive inhibitor of a Clq protein). An antagonist need not directly bind, or compete with, the ligand in order to modulate signal transduction via the $ClqR_P$ pathway.

"Formulation" means a composition capable of gene delivery and gene expression, that is, capable of delivering a nucleotide sequence to, or directly into, a target cell whereupon the formulation containing the nucleotide sequence is incorporated on the cytoplasmic side of the outermost membrane of the target cell and capable of achieving gene expression so that detectable levels of gene expression of the delivered nucleotide sequence are expressed in the target cell. More preferably, after delivery into the cytoplasmic side of the cell membrane the composition is subsequently transported, without undergoing endosomal or lytic degradation, into the nucleus of the target cell in a functional state capable of achieving gene expression so that detectable levels of gene expression of the delivered nucleotide sequence are expressed in the target cell. Expression levels of the gene or nucleotide sequence inside the target cell are capable of providing gene expression for a duration of time and in an amount such that the nucleotide product therein is capable of providing a biologically beneficially effective amount of gene product or in such an amount as to provide a functionally beneficial biological effect on the target cell. As used herein, the term formulation can refer to, but is not limited by (either explicitly or implicitly) the following examples: (1) liposome or liposome formulations or liposomal compositions either cationic, anionic or neutral in net character and net charge; (2) DNA, nucleic acid or a nucleic acid expression vector ionically complexed with a polycation/s and a ligand/s such that after attachment of the [DNA+Polycation+Ligand] composition to a cell surface receptor on a target cell via the ligand, the [DNA+Polycation+Ligand] composition is capable of being endocytosed into the target cell and the DNA is subsequently decoupled from the ligand and polycation and delivered to the cell nucleus in a functional condition for subsequent expression. Various alterations in the composition can be envisioned by those of ordinary skill in the art such as including peptide sequences which (a) protect the composition from endosomal lysis after incorporation into the target cell by allowing the composition to leave the lysosomal vesicle, or (b) which act as a nuclear targeting agent, chaperoning the nucleic acid through the pores of the nuclear envelope and into the nucleus of the cell. Similar formulations, which have been previously described, are the asialoglycoprotein-polylysine conjugation (Wu and Wu, *J. Biol. Chem.* 263:14621, 1988; Wu et al., *J. Biol. Chem.* 264:16985, 1989); One of ordinary skill in the art would realize that the Clq ligand could be adopted to such formulations to enhance gene delivery to endothelial cells, macrophages and monocytes; (3) naked nucleic acid; (4) compacted nucleic acid or a compacted formulation; or (5) plasmid or naked DNA which can be microinjected (Wolff et al., *Science* 247:1465, 1990); (6) nucleic acid in a viral or retroviral vector compositions; and (7) colloidal dispersions (Felgner et al., *Proc. Natl. Acad. Sci. USA* 84:7413, 1987; Ono et al., *Neuroscience Lett.* 117:259, 1990; Brigham et al., *Am. J. Med. Sci.* 298:278, 1989; Staubinger and Papahadjopoulos, *Meth. Enz.* 101:512, 1983). One of ordinary skill in the art will recognize that other compositions for the delivery of nucleotide sequences to target cells may be envisioned.

"Gene delivery" means transportation or transfer of a composition or formulation inside of or into contact with a target cell so that the composition or formulation is capable of being taken up by means of a cytotic process (i.e., pinocytosis, endocytosis, phagocytosis, macrocytosis etc.) into the interior or cytoplasmic side of the outermost cell membrane of the target cell where it can subsequently be transported into the nucleus of the cell in such functional condition that it is capable of achieving detectable gene expression for a period of time and in such an amount to produce a detectable biologically beneficial effect.

"Gene expression" means the process, after delivery into a target cell, by which a nucleotide sequence undergoes successful transcription and translation such that detectable levels of the delivered nucleotide sequence are expressed in an amount and over a time period so that a functional biological effect is achieved. As used herein, gene expression can refer to, but is not restricted by (either explicitly or implicitly) the following examples. A ClqR$_P$ nucleic acid sequence is delivered and expressed in targeted cells such that the targeted cells increase, decrease, or are inhibited in the production of ClqR$_P$ protein or ClqR$_P$ RNA, thus: either enhancing phagocytosis, inhibiting phagocytosis, enhancing the complement portion of the immune system or dampening the complement portion of the immune system and subsequently leading to a beneficially detectable biological effect or outcome.

"Expressible genetic construct" means a construct which has the ClqR$_P$ gene positioned for expression.

"Operably linked" means that a gene and a regulatory sequence(s) are connected to permit expression of the ClqR$_P$ gene when the appropriate molecules (e.g., transcriptional activator proteins) are bound to the regulatory sequence(s).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extrachromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

"Promoter" means the minimal nucleotide sequence sufficient to direct transcription. Also included in the invention are those promoter elements that are sufficient to render promoter-dependent gene expression controllable for cell-type specific, tissue specific, or inducible by external signals or agents; such elements may be located in the 5' or 3' regions of the native gene.

"Detectably-labeled" means any means for marking and identifying the presence of a molecule, e.g., an oligonucleotide probe or primer, an antibody or fragment thereof, a protein or fragment thereof, a gene or fragment thereof, or a cDNA molecule. Methods for detectably-labeling are well known in the art and include, without limitation, radioactive labeling (e.g, with an isotope such as $^{32}P$ or $^{35}S$) and nonradioactive labeling (e.g., chemiluminescent labeling, fluorescent labeling).

"Purified antibody" means antibody which is at least 60%, by weight, free from proteins and naturally-occurring organic molecules with which it is naturally associated. Preferably, the preparation is at least 75%, more preferably 90%, and most preferably at least 99%, by weight, antibody, e.g., a $ClqR_P$ specific antibody. A purified antibody may be obtained, for example, by affinity chromatography using recombinantly-produced protein or conserved motif peptides and standard techniques. The invention can employ not only intact monoclonal or polyclonal antibodies, but also an immunologically-active antibody fragment, such as a Tab, Fab' or $(Fab')_2$ fragment, or a genetically engineered Fv fragment (Ladner et al., U.S. Pat. No. 4,946,788).

"Specifically binds" means an antibody which recognizes and binds a specified protein but which does not substantially recognize and bind other molecules in a sample, e.g., a biological sample, which naturally includes protein.

Due to the expression of $ClqR_P$ in immune cells and tissue, there are a variety of applications using the polypeptide, polynucleotide, and antibodies of the invention, related to these cells or tissues. Such applications include treatment of disorders involving either the complement component of the immune system or immunodeficiencies. In addition, $ClqR_P$ may be useful in various gene delivery and expression procedures, such as to enhance nucleotide uptake by endothelial cells and macrophages/monocytes.

"Therapeutically effective" as used herein, refers to an amount of formulation that is of sufficient quantity to ameliorate the state of the patient so treated. "Ameliorate" refers to a lessening of the detrimental effect of the disease state or disorder in the patient receiving the therapy. The subject of the invention is preferably a human, however, it can be envisioned that any animal can be treated in the method of the instant invention. The term "modulate" means enhance, inhibit, alter, or modify the expression or function of $ClqR_P$ mRNA, nucleic acid, polypeptide or protein.

Methods known to one of ordinary skill in the art for detecting a change in signal transduction in a cell via an extracellular receptor can be used in the invention. In one preferred embodiment, a change in signal transduction can be detected as a change in inositol phosphate levels in a cell. In another preferred embodiment, an intracellular calcium signal that is induced by activation via the $ClqR_P$ can be measured with fluorescent calcium indicators, such as fluor3, or fura2. Such methods are well known to those of ordinary skill in the art.

The invention also provides a method for determining whether a test agent or composition modulates signal transduction in a cell. The method can be performed by (i) providing a cell that has a $ClqR_P$; (ii) contacting the cell with a test agent or composition and a ligand that, in the absence of the test agent or composition, activates the $ClqR_P$ in the cell; and (iii) detecting a change in the cell. In practicing the invention, the cell can be contacted with the test agent or composition and ligand either simultaneously or sequentially. An increase in signal transduction indicates that the test agent or composition is an agonist of the $ClqR_P$ while a decrease in signal transduction indicates that the test agent or composition is an antagonist of the $ClqR_P$. If desired, the above-described method for identifying ligands can be used to identify ligands of $ClqR_P$ for use in this aspect of the invention. Any agent or composition can be used as a test agent or composition in practicing the invention; a preferred test agent or composition includes polypeptides and small organic agent or compositions. Although sequence or structural homology can provide a basis for suspecting that a test agent or composition can modulate the $ClqR_P$ in a cell, randomly chosen test agent or compositions also are suitable for use in the invention. Art-known methods for randomly generating an agent or compositions (e.g., expression of polypeptides from nucleic acid libraries) can be used to produce suitable test agent or compositions. Those skilled in the art will recognize alternative techniques can be used in lieu of the particular techniques described herein.

The invention also provides a method for detecting novel ligands which bind $ClqR_P$ which comprises contacting a sample comprising the $ClqR_P$ with test compositions and measuring the interaction of the receptor with the test composition.

The $ClqR_P$ protein of the instant invention is useful in a screening method for identifying test compounds or test compositions which affect the binding to the $ClqR_P$. Thus, in another embodiment, the invention provides a method for screening test compositions comprising incubating components, which include the test composition, the $ClqR_P$ and the ligand of the $ClqR_P$, under conditions sufficient to allow the components to interact, then subsequently measuring the effect the test composition has on the formation of the affinity complex. Such screening identification can be supplied in the form of a kit as discussed above. The observed effect on the formation of the affinity complex between the $ClqR_P$ and its ligand may be either agonistic or antagonistic. Preferably, the polypeptide encoding the $ClqR_P$ is the polypeptide or functional fragment thereof of SEQ ID NO: 2, or a synthetic peptide which has the biological activity of the $ClqR_P$ protein. Methods for measuring the effect of the composition on the binding of the ligand to the $ClqR_P$ will be known to those of ordinary skill in the art. For example, the effect of binding of a ligand to the $ClqR_P$ can be analyzed by measuring the internalization of radiolabeled or photoaffinity labeled Clq protein.

The invention also includes fragments of $ClqR_P$ polypeptides, that retain at least one $ClqR_P$-specific activity or epitope. For example, a $ClqR_P$ polypeptide fragment containing, e.g., at least 8–10 amino acids, can be used as an immunogen in the production of $ClqR_P$-specific antibodies. Such fragments can easily be identified by comparing the sequence of $ClqR_P$ by reference to FIG. 3. In addition to their use as peptide immunogens, $ClqR_P$ fragments can be used in immunoassays, such as ELISAs, to detect the presence of $ClqR_P$-specific antibodies in samples.

The $ClqR_P$ polypeptides of the invention can be obtained using any of several standard methods. For example, $ClqR_P$ polypeptides can be produced in a standard recombinant expression systems (see below), chemically synthesized (this approach may be limited to small $ClqR_P$ peptide fragments), or purified from tissues in which they are naturally expressed (see, e.g., Ausubel, et al., supra).

The invention also provides isolated nucleic acid molecules that encode the $ClqR_P$ polypeptides described above, as well as fragments thereof. These nucleic acids can contain naturally occurring nucleotide sequences (see FIG. 3), or sequences that differ from those of the naturally occurring nucleic acids that encode $ClqR_P$s, but encode the same amino acids, due to the degeneracy of the genetic code or amino acids which are conservative variations. The nucleic acids of the invention can contain DNA or RNA nucleotides, or combinations or modifications thereof.

The nucleic acid molecules of the invention can be used as templates in standard methods for production of $ClqR_P$ gene products (e.g., $ClqR_P$ and $ClqR_P$ polypeptides; see below). In addition, the nucleic acid molecules that encode $ClqR_P$ polypeptides (and fragments thereof) and related nucleic acids, such as (1) nucleic acids containing sequences that are complementary to, or that hybridize to, nucleic acids encoding $ClqR_P$ polypeptides, or fragments thereof (e.g., fragments containing at least 9, 12, 15, 20, or 25 nucleotides); and (2) nucleic acids containing sequences that hybridize to sequences that are complementary to nucleic acids encoding $ClqR_P$ polypeptides, or fragments thereof (e.g., fragments containing at least 9, 12, 15, 20, or 25 nucleotides); can be used in methods focused on their hybridization properties. For example, as is described in further detail below, such nucleic acid molecules can be used in the following methods: PCR methods for synthesizing $ClqR_P$ nucleic acids, methods for detecting the presence of a $ClqR_P$ nucleic acid in a sample, screening methods for identifying nucleic acids encoding new $ClqR_P$ family members, and therapeutic methods.

The invention also includes methods for identifying nucleic acid molecules that encode members of a $ClqR_P$ polypeptide family. In these methods, a sample, e.g., a nucleic acid library, such as a cDNA library, that contains a nucleic acid encoding a $ClqR_P$ polypeptide is screened with a $ClqR_P$-specific probe, e.g., a $ClqR_P$-specific nucleic acid probe. $ClqR_P$-specific nucleic acid probes are nucleic acid molecules (e.g., molecules containing DNA or RNA nucleotides, or combinations or modifications thereof) that specifically hybridize to nucleic acids encoding $ClqR_P$ polypeptides, or to complementary sequences thereof. The term "$ClqR_P$-specific probe," in the context of this method of invention, refers to probes that bind to nucleic acids encoding $ClqR_P$ polypeptides, or to complementary sequences thereof, to a detectably greater extent than to nucleic acids encoding homologous $ClqR_P$ receptor family sequences, or to complementary sequences thereof. The term "$ClqR_P$-specific probe" thus includes probes that can bind to nucleic acids encoding $ClqR_P$ polypeptides (or to complementary sequences thereof), but not to nucleic acids encoding homologous $ClqR_P$ receptor family sequences (or to complementary sequences thereof), to an appreciable extent.

The invention facilitates production of $ClqR_P$-specific nucleic acid probes. Methods for obtaining such probes can be designed based on the amino acid sequence alignments shown in FIG. 3. The probes, which can contain at least 9, e.g, at least 12, 15, 25, 35, 50, 100, or 150 nucleotides, can be produced using any of several standard methods (see, e.g., Ausubel, et al., supra). For example, preferably, the probes are generated using PCR amplification methods, such as those described below. In these methods, primers are designed that correspond to $ClqR_P$ sequences, which can include $ClqR_P$-specific amino acids, and the resulting PCR product is used as a probe to screen a nucleic acid library, such as a cDNA library.

As is known in the art, PCR primers are typically designed to contain at least 15 nucleotides, for example 15–30 nucleotides. The design of $ClqR_P$-specific primers containing 21 nucleotides, which encode $ClqR_P$ peptides containing 7 amino acids, are described as follows. Preferably, most or all of the nucleotides in such a probe encode $ClqR_P$-conserved amino acids, including $ClqR_P$-specific amino acids. For example, primers containing sequences encoding for at least 40% $ClqR_P$-conserved amino acids can be used. Such a primer, containing 21 nucleotides, can include nucleotide sequences encoding for at least 3 out of 7 $ClqR_P$-conserved amino acids or 4 out of 7, or 5 out of 7 $ClqR_P$-conserved amino acids. As can be determined by analysis of FIG. 3, in the case of a 21 nucleotide primer, encoding 7 amino acids, up to 5 amino acids can be $ClqR_P$-specific. Thus, the primer can contain sequences encoding at least one $ClqR_P$-specific amino acid, for example, up to 5 $ClqR_P$-specific amino acids. Once $ClqR_P$-specific amino acid sequences are selected as templates against which primer sequences are to be designed, the primers can be synthesized using, e.g., standard chemical methods. As is described above, due to the degeneracy of the genetic code, such primers should be designed to include appropriate degenerate sequences, as can readily be determined by one skilled in the art.

Based on the guidelines presented above, examples of ClqR$_P$-conserved amino acid peptides that can be used as templates for the design of ClqR$_P$-specific primers are as follows. Additional examples can be found by analysis of sequence alignments of ClqR$_P$ polypeptides. Primers can be designed, for example, based on 5–10 amino acid regions of the ClqR$_P$ peptide, depending on the lengths of the primers desired. For example, primers can be designed to correspond to 7 consecutive amino acids of any of the segments shown below:

```
1. P-K-Y-G-C-N-F-N-N-G-G-C-H-Q-D-C-F-C-G-G-D-G-S-F-L-C-G         (SEQ ID NO:3)
   C-R-P-G-F-R-L-L-D-D-L-V-T-C-A
   (corresponding to amino acids 260-301 of human ClqR_pEGF 1

2. S-R-N-P-C-S-S-S-P-C-R-G-G-A-T-C-V-L-G-P-H-G-K-N-Y-T-C-R-C-P   (SEQ ID NO:4)
   Q-G-Y-Q-L-D-S-S-Q-L-D-C-V
   (corresponding to amino acids 302-344 of human ClqR_p-EFG-2)

3. D-V-D-E-C-Q-D-S-P-C-A-Q-E-C-V-N-T-P-G-G-F-R-C-E-C-W-V-G-Y     (SEQ ID NO:5)
   E-P-G-G-P-G-E-G-A-C-Q
   (corresponding to amino acids 345-384 of human ClqR_p-EFG-3)

4. G-G-P-G-Q-V-T-Y-T-P-F-Q-T-T-S-S-S-L-E-A-V-P-F-A-S-A-A-N-V     (SEQ ID NO:6)
   A-C-G-E
   (corresponding to amino acids 194-227 of human ClqR_p-1) For
   example, a specific primer based on this PCR product, SEQ ID NO:80,
   5'CAAGGAGGAACTGGTGGTCTGG-3', and a degenerate primer based on
   the sequenced amino terminus starting at amino acid 2,
   5'GGIGClGA(tc)ACIGA(ag)GC-3', were designed and used to
   amplify by RT PCR a cDNA corresponding to the amino terminus
   of the ClqR_pprotein from U937 cDNA.

5. D-V-D-E-C-A-L-G-R-S-P-C-A-Q-G-C-T-N-T-D                       (SEQ ID NO:7
   G-S-F-H-C-S-C-E-E-G-Y-V-L-A-G-E-D-G-T-Q-C-Q;
   corresponding to amino acids 385-426 of human ClqR_p-EGF-4)

6. L-L-L-F-Y-I-L-G-T-V-V-A-I-L-L-L-A-L-A-L-G-L-L-V               (SEQ ID NO:8)
   (corresponding to amino acids 581-605 of human ClqR_p-Transmembrane)

7. D-V-D-E-C-V-G-P-G-G-P-L-C-D-S-L-C-F-N-T-Q-G-S-F-H-C-G-C-L     (SEQ ID NO:9)
   P-G-W-V-L-A-P-N-G-V-S-C-T;
   corresponding to amino acids 427-468 of human ClqR_p-EGF-5)

8. Y-R-K-R-E-E-K-K-E-K-P-Q-N-A-A-D-S-Y-S-W-V-P-E                 (SEQ ID NO:10)
   R-A-E-S-R-A-M-E-N-Q-Y-S-P-T-P-G-T-D-C;
   corresponding to amino acids 606-652 of human ClqR_p-cytoplasmic-tail)
```

As is described above, ClqR$_P$-specific primers, for example primers based on the ClqR$_P$-specific peptides shown above, or portions thereof, can be used in PCR reactions to generate ClqR$_P$-specific probes, which can be used in standard screening methods to identify nucleic acids encoding ClqR$_P$ family members (see, e.g., Ausubel, et al., supra).

In addition to ClqR$_P$-specific nucleic acid probes, ClqR$_P$-specific polypeptide probes, such as ClqR$_P$-specific antibodies, can be used to screen samples, e.g., expression libraries, for nucleic acids encoding novel ClqR$_P$ polypeptides, or portions thereof. For example, an antibody that specifically binds to a ClqR$_P$-specific peptide can be used in this method. Methods for carrying out such screening are well known in the art (see, e.g., Ausubel, et al., supra).

The sequences of a pair of nucleic acid molecules (or two regions within a single nuclenucleic acid molecule) are said to be "complementary" to each other if base pairing interactions can occur between each nucleotide of one of the members of the pair and each nucleotide of the other member of the pair. A pair of nucleic acid molecules (or two regions within a single nucleic acid molecule) are said to "hybridize" to each other if they form a duplex by base pairing interactions between them. As is known in the art, hybridization between nucleic acid pairs does not require complete complementarity between the hybridizing regions, but only that there is a sufficient level of base pairing to maintain the duplex under the hybridization conditions used.

Hybridization reactions are typically carried out under low to moderate stringency conditions, in which specific and some non-specific interactions can occur. After hybridization, washing can be carried out under moderate or high stringency conditions to eliminate non-specific binding. As is known in the art, optimal washing conditions can be determined empirically, e.g., by gradually increasing the stringency. Condition parameters that can be changed to affect stringency include, e.g., temperature and salt concentration. In general, the lower the salt concentration and the higher the temperature, the higher the stringency. For example, washing can be initiated at a low temperature (e.g., room temperature) using a solution containing an equivalent or lower salt concentration as the hybridization solution. Subsequent washing can be carried out using progressively warmer solutions having the same salt solution. Alternatively, the salt concentration can be lowered and the temperature maintained in the washing step, or the salt concentration can be lowered and the temperature increased. Additional parameters can be altered to affect stringency, including, e.g, the use of a destabilizing agent, such as formamide.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

The nucleic acid molecules of the invention can be obtained by any of several standard methods. For example, the molecules can be produced using standard recombinant, enzymatic (e.g., PCR or reverse transcription (RT)/PCR methods), and chemical (e.g., phosphoramidite-based synthesis) methods. In addition, they can be isolated from samples, such as nucleic acid libraries and tissue samples, using standard hybridization methods. For example, as described above, using standard methods, genomic or cDNA libraries can be hybridized with nucleic acid probes corresponding to $ClqR_P$ nucleic acid sequences to detect the presence of a homologous nucleotide sequence in the library (see, e.g., Ausubel, et al., supra). These methods are described in more detail above. Also as described above, nucleic acids encoding polypeptides containing at least one $ClqR_P$ epitope, such as a $ClqR_P$-specific epitope, can also be identified by screening a cDNA expression library, such as a library contained in lambda gt11, with a $ClqR_P$-specific antibody as a probe. Such antibodies can be either polyclonal or monoclonal and are produced using standard methods (see, e.g., Harlow and Lane, *Antibodies: A Laboratory Manual*, Cold Spring Harbor Laboratory Press, Cold Spring Harbor, N.Y., 1988).

$ClqR_P$-specific antibodies and nucleic acids can be used as probes in methods to detect the presence of a $ClqR_P$ polypeptide (using an antibody) or nucleic acid (using a nucleic acid probe) in a sample, such as a biological fluid (e.g., synovial fluid, such as an arthritic joint) or a tissue sample (e.g., CNS tissue, thymus tissue or endothelial tissue). In these methods, a $ClqR_P$-specific antibody or nucleic acid probe is contacted with a sample from a patient suspected of having a $ClqR_P$-associated disorder, and specific binding of the antibody or nucleic acid probe to the sample detected. The level of $ClqR_P$ polypeptide or nucleic acid present in the suspect sample can be compared with the level in a control sample, e.g, an equivalent sample from an unaffected individual, to determine whether the patient has a $ClqR_P$-associated disorder. $ClqR_P$ polypeptides, or fragments thereof, can also be used as probes in diagnostic methods, for example, to detect the presence of $ClqR_P$-specific antibodies in samples. Additionally, $ClqR_P$-specific antibodies could be used to detect novel ligands which have formed an affinity complex with a $ClqR_P$ receptor or fragment thereof.

The $ClqR_P$-specific nucleic acid probes can be labeled with a compound that facilitates detection of binding to the $ClqR_P$ nucleic acid in the sample. For example, the probe can contain biotinylated nucleotides, to which detectably labeled avidin conjugates (e.g., horse-radish peroxidase-conjugated avidin) can bind. Radiolabeled nucleic acid probes can also be used. These probes can be used in nucleic acid hybridization assays to detect altered levels of $ClqR_P$s in a sample. For example, in situ hybridization, RNase protection, and Northern Blot methods can be used. Other standard nucleic acid detection methods that can be used in the invention are known to those of skill in the art (see, e.g., Ausubel, et al., supra). In addition, when the diagnostic molecule is a nucleic acid, it can be amplified prior to binding with a $ClqR_P$-specific probe. Preferably, PCR is used, but other nucleic acid amplification methods, such as the ligase chain reaction (LCR), ligated activated transcription (LAT), and nucleic acid sequence-based amplification (NASBA) methods can be used.

Additionally, $ClqR_P$-specific nucleic acid probes could be used to detect unique polypeptide expression clones from nucleic acid libraries such as expression libraries for fragments of the $ClqR_P$ nucleic acid sequence or homologues of the $ClqR_P$ nucleic acid sequence. $ClqR_P$-specific nucleic acid probes could be used to detect expression clones used to randomly generate compounds (e.g., expression of polypeptides from nucleic acid libraries) that can be used to produce suitable test compounds of the instant invention. A cDNA expression library can be screened indirectly for $ClqR_P$ peptides having at least one epitope, using antibodies specific for $ClqR_P$ as described herein. Such antibodies can be either polyclonally or monoclonally derived and used to detect expression product indicative of the presence of $ClqR_P$ cDNA.

Specifically disclosed herein is a 3.46 Kb cDNA sequence containing the active portion of the human $ClqR_P$ coding sequence. The cDNA clone from which this sequence was obtained contains the entire coding sequence for $ClqR_P$. The amino acid sequence disclosed includes a C-type carbohydrate recognition domain at the N-terminus, five Epidermal Growth Factor (EGF)-like domains, including three calcium binding (cb) EGF domains, a single transmembrane (TM) domain and a cytotaismic tail. A putative N-linked glycosylation site is located within the second EGF domain at amino acid position N325. The predicted molecular weight of the mature protein Clq based on the amino acid sequence is 66,495 Da. The cDNA and deduced amino acid sequence of $ClqR_P$ are shown in FIG. 3. Nucleotides and amino acids are numbered based on the initiator methionine.

The polynucleotide encoding $ClqR_P$ includes the nucleotide sequence in FIG. 3 (SEQ ID NO.: 1), as well as nucleic acid sequences complementary to that sequence. A complementary sequence may include an antisense nucleotide. When the sequence is RNA, the deoxynucleotides A, G, C, and T of FIG. 3 are replaced by ribonucleotides A, G, C, and U, respectively. Also included in the invention are fragments of the above-described nucleic acid sequences that are at least 9 bases in length, which is sufficient to permit the fragment to selectively hybridize to DNA that encodes the protein of FIG. 3 (SEQ ID NO.: 1) under physiological conditions.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features. Therefore, given a partial DNA sequence of the gene of interest, one of skill in the art would be able to prepare probes for isolation of a full length cDNA clone, without undue experimentation (see e.g., Ausubel, et al., *Current Protocols in Molecular Biology*, Units 6.3–6.4, Greene Publ., current edition; Maniatis, et al., *Molecular Cloning*, Cold Spring Harbor Laboratories, current edition).

The development of specific DNA sequences encoding $ClqR_P$ can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

DNA sequences encoding $ClqR_P$ can be expressed in vitro, in vivo or ex vivo by DNA transfer into a suitable target cell. "Target cells" are cells in which a vector can be propagated and its DNA expressed or in which a formulation can be delivered into a cell for subsequent gene expression. The term also includes any progeny of the subject target cell. It is understood that all progeny may not be identical to the parental cell since there may be mutations that occur during replication. However, such progeny are understood to be included when the term "target cell" is used. Methods of stable transfer, meaning that the foreign DNA is continuously maintained in the host, are known in the art. Determination of $ClqR_P$ mRNA expression levels in targeted cells can be determined by one of ordinary skill in the art by comparing either or both $ClqR_P$ RNA or $ClqR_P$ protein levels before and after treatment of the target cells. Such methods of analysis employing techniques like Northern or Western analysis are common in the art. Other common techniques to determine levels of RNA or protein in such $ClqR_P$ target cells will be known to those in the art.

In the present invention, the $ClqR_P$ polynucleotide sequences may be inserted into a recombinant expression vector. The term "recombinant expression vector" refers to a plasmid, virus or other vehicle known in the art that has been manipulated by insertion or incorporation of the $ClqR_P$ genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., *Gene* 56:125, 1987), the pMSXND expression vector for expression in mammalian cells (Lee and Nathans, *J. Biol. Chem.* 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding $ClqR_P$ can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a target cell are known in the art. Such vectors are used to incorporate DNA sequences of the invention.

Transformation of a target cell with recombinant DNA may be carried out by conventional techniques as are well known to those skilled in the art. Where the target is prokaryotic, such as *E. coli*, competent cells which are capable of DNA uptake can be prepared from cells harvested after their exponential growth phase and subsequently treated by the $CaCl_2$ method using procedures well known in the art. Alternatively, $MgCl_2$ or RbCl can be used. Transformation can also be performed after forming a protoplast of the target cell if desired.

When the target cell is a eukaryote, such methods of transfection of DNA as calcium phosphate co-precipitates, conventional mechanical procedures such as microinjection, electroporation, insertion of a plasmid encased in liposome or liposome formulations, or virus vectors may be used. Eukaryotic cells can also be co-transformed with DNA sequences encoding the $ClqR_P$ of the invention, and a second foreign DNA molecule encoding a selectable phenotype, such as the herpes simplex thymidine kinase gene. Another method of transformation is to use a eukaryotic viral vector, such as simian virus 40 (SV40) or bovine papilloma virus, to transiently infect or transform eukaryotic cells and express the protein. (see e.g., *Eukaryotic Viral Vectors*, Cold Spring Harbor Laboratory, Gluzman ed., 1982).

Isolation and purification of microbial expressed $ClqR_P$ polypeptide, or fragments, or conservative variants thereof, provided by the invention, may be carried out by conventional means including preparative chromatography and immunological separations involving monoclonal or polyclonal antibodies.

The $ClqR_P$ polypeptides of the invention can also be used to produce antibodies which are immunoreactive or bind to epitopes of $ClqR_P$ polypeptides. Antibody which consists essentially of pooled monoclonal antibodies with different epitopic specificities, as well as distinct monoclonal antibody preparations are provided. Monoclonal antibodies are made from antigen containing fragments of the $ClqR_P$ protein by methods well known in the art (Kohler et al., *Nature* 256:495, 1975; *Current Protocols in Molecular Biology*, Ausubel et al., ed., 1989).

The term "antibody" as used in this invention includes intact molecules as well as fragments thereof, such as Fab, Fab', $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, N.Y. (current edition), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the $ClqR_P$ polypeptide of the invention can be prepared using an intact polypeptide or fragments containing small peptides of interest as the immunizing antigen. The polypeptide or peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, rat, goat, sheep or rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See e.g., Coligan, et al., Unit 9, *Current Protocols in Immunology*, Wiley Interscience, current edition, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

The present invention identifies a nucleotide sequence that can be expressed in an altered manner as compared to expression in a normal cell, therefore it is possible to design appropriate therapeutic or diagnostic techniques directed to this sequence. Thus, where a disorder is associated with the altered expression of $ClqR_P$, nucleic acid sequences that interfere with $ClqR_P$ expression at the transcriptional or translational level can be used. This approach utilizes, for example, antisense, missense or nonsense, nucleic acid and ribozymes to block translation of a specific $ClqR_P$ mRNA, either by masking that mRNA with an antisense nucleic acid or by cleaving it with a ribozyme. Such $ClqR_P$ disorders may include diseases such as vasculitis and sepsis, for example. One of ordinary skill in the art can determine without undue experimentation if the delivery and expression of $ClqR_P$ mRNA in target cells has altered the level of $ClqR_P$ polypeptide or nucleic acid by comparing the levels of $ClqR_P$ polypeptide or nucleic acid present in $ClqR_P$ target cells before and after treatment or by comparing target cells with equivalent non-target controls. Such techniques as Northern or Western analysis are common to those in the art and would be useful in making such determinations. Although, other techniques useful for such comparisons are commonly known to one of ordinary skill in the art.

Antisense nucleic acids are DNA or RNA molecules that are complementary to at least a portion of a specific MRNA molecule (Weintraub, *Scientific American* 262:40, 1990). In the cell, antisense nucleic acids hybridize to a corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target $ClqR_P$-producing cell. The use of antisense methods to inhibit the in vitro translation of genes is well known in the art (Marcus-Sakura, *Anal. Biochem.* 172:289, 1988).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *Amer. Med. Assn.* 260: 3030, 1988). A major advantage of this approach is that, because they are sequence-specific, only mRNAs with particular sequences are inactivated.

The present invention also provides gene delivery and gene expression for disorders mediated by $ClqR_P$ protein. Such gene delivery and gene expression achieves its beneficial effect by altering the levels of $ClqR_P$ mRNA in a cell. This may entail delivery and expression of $ClqR_P$ antisense to target cells or the delivery and expression of heterologous $ClqR_P$ receptors to target cells to enhance the function of the Clq component of the immune system. Delivery and expression of $ClqR_P$ nucleic acid can be achieved by a variety of means known to those in the art. A preferred means is using a recombinant expression vector such as a chimeric virus or a colloidal dispersion system. Especially preferred for therapeutic delivery of antisense sequences is the use of formulations containing liposome or liposome formulations or liposomal-like agents capable of being targeted to particular cells or receptors. Various viral vectors which can be utilized for gene therapy as taught herein include adenovirus, herpes virus, vaccinia, or, preferably, an RNA virus such as a retrovirus.

Another targeted delivery system for $ClqR_P$ antisense polynucleotides is a colloidal dispersion system. Colloidal dispersion systems include macromolecule complexes, nanocapsules, microspheres, beads, and lipid-based systems including oil-in-water emulsions, micelles, mixed micelles, and liposome or liposome formulations. The preferred colloidal system of this invention is a liposome or liposomal formation. Liposome or liposome formulations are artificial membrane vesicles or formulations containing liposomal compositions that can be complexed with other compositions. These formulations may have net cationic, anionic or neutral charge characteristics are useful characteristics with in vitro, in vivo and ex vivo delivery methods.

It has been shown that large unilamellar vesicles (LUV), which range in size from 0.2–4.0 $\mu$m can encapsulate a substantial percentage of an aqueous buffer containing large macromolecules. RNA, DNA and intact virions can be encapsulated within the aqueous interior and be delivered to cells in a biologically active form (Fraley et al., *Trends Biochem. Sci.* 6:77, 1981). Additionally, non-membrane bound liposomal formulations can be used for delivery and expression of nucleic acids (Felgner et al., *Proc. Natl. Acad. Sci. USA* 84: 7413, 1987). In addition to mammalian cells, liposome or liposome formulations have been used for delivery of polynucleotides in plant, yeast and bacterial cells. For a liposome or liposome formulation to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle or of the nucleic acid of the formulation to the target cell cytoplasm at high efficiency without degradation and in a functional state capable of permitting gene expression at such levels as to achieve a detectable biological effect; and (4) accurate and effective expression of genetic information which has been delivered (Mannino et al., *Biotechniques* 6:682, 1988).

A well-characterized "on/off" switch for use in a recombinant expression vector is the antibiotic (tetracycline) regulated promoter system. Means for construction of such a system are well-known in the art; for review in this regard, those of skill in the art may wish to consult Furth et al., *Proc. Natl. Acad. Sci. USA,* 91:9302, 1994 (tetracycline regulated control of gene expression in transgenic mice).

In addition, a transgenic animal model can be developed which is especially predictive of the impact on the defense/clearance system in which $ClqR_P$ activity has been increased or decreased according to the method of the invention. Protocols useful in producing such $ClqR_P$ transgenic animals are described below. The protocol generally follows conventional techniques for introduction of expressible transgenes into mammals. Those of ordinary skill in the art will be familiar with these applications and will be able to apply the techniques in the context of the present invention without undue experimentation.

For example, embryonal target cells at various developmental stages can be used to introduce transgenes. Different methods are used depending on the stage of development of the embryonal target cell. The zygote is the best target for microinjection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al., *Proc. Natl. Acad. Sci. USA* 82:4438, 1985). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce transgene ipto a non-human animal. The developing non-human embryo can be cultured in vitro to the blastocyst stage. During this time, the blastomeres can be targets for retroviral infection (Jaenisch, *Proc. Natl. Acad. Sci. USA* 73:1260, 1976). Efficient infection of the blastomeres is obtained by enzymatic treatment to remove the zona pellucida (Hogan, et al., *Manipulating the Mouse Embryo*, Cold Spring Harbor Laboratory Press, Cold Spring Harbor, N.Y., 1986). The viral vector system used to introduce the transgene is typically a replication-defective retrovirus carrying the transgene (Jahner et al., *Proc. Natl. Acad Sci. USA* 82:6927, 1985; Van der Putten et al., *Proc. Natl. Acad. Sci. USA* 82: 6148, 1985). Transfection is easily and efficiently obtained by culturing the blastomeres on a monolayer of virus-producing cells (Van der Putten supra, Steward et al., *EMBO J.* 6: 383, 1987).

Alternatively, infection can be performed at a later stage. Virus or virus-producing cells can be injected into the blastocoele (Jahner et al., *Nature* 298: 623, 1982). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line, albeit with low efficiency, by intrauterine retroviral infection of the midgestation embryo (Jahher et al., supra).

A third type of target cell for introduction of heterologous $ClqR_P$ nucleic acid sequences is the embryonal stem cell (ES). ES cells are obtained from preimplantation embryos cultured in vitro and fused with embryos (Evans et al., *Nature* 292:154, 1981; Bradley et al., *Nature* 309: 255, 1984; Gossler et al., *Proc. Natl. Acad. Sci. USA* 83:9065, 1986; and Robertson et al., *Nature* 322:445, 1986). Transgenes can be efficiently introduced into the ES cells by DNA transfection or by retrovirus-mediated transduction. These transformed ES cells can thereafter be combined with blastocysts from a non-human animal. The ES cells will thereafter colonize the embryo and contribute to the germ line of the resulting chimeric animal (see for review, Jaenisch, *Science* 240:1468, 1988).

Construction of $ClqR_P$ transgenes can be performed by those of ordinary skill in the art using the teachings concerning the $ClqR_P$ nucleotide sequences herein. One of ordinary skill in the art can "knock out" the $ClqR_P$ enhancement of phagocytic function in mice by targeted disruption of the murine $ClqR_P$ gene. This can be accomplished by homologous recombination in murine embryonic stem (ES) cells using standard techniques. The clinical and cellular consequences of targeted disruption of $ClqR_P$ can be investigated in multiple genetic backgrounds including inbred strains, strains with many undefined nonsense alleles, and strains of known mutant genotype to determine if: (a) targeted disruption of $ClqR_P$ can effect a loss of the $ClqR_P$ derived enhancement of phagocytic function; (b) loss of the $ClqR_P$ enhancement of host defense and clearance of cellular or foreign debris can have an phenotype consequences (i.e., the creation of knockout phenotypes), (c) loss of the $ClqR_P$ enhancement of phagocytic function unmasks the effects of other complement components heretofore unknown.

Transgenic murine cells can be generated by using a vector for $ClqR_P$ gene targeting by homologous recombination. The vector contains a large genomic fragment of the murine $ClqR_P$ gene. The exons can be deleted and substituted for by a Neomycin resistance expression cassette. A thymidine kinase gene can be inserted at the end of the long arm of homology to assist in the selection of bona fide-homologous recombinants. Transfection and stable selection of murine SV/129 cells will allow identification of a clonal colony of cells harboring one inactivated $ClqR_P$ allele. These cells can be injected into mouse blastocysts to create chimeras. Chimeras can be bred to yield animals heterozygous for the targeted allele. Finally, heterozygotes can be bred to create homozygotes. Mice with characterized phenotypes can be bred to mice deficient for the $ClqR_P$ enhancement of phagocytic function. If necessary, the identical approach of homologous recombination-based targeting of endogenous genes can then be used in cultured human cells. This would require a second phase of transfection and selection, using a different selectable marker, to target both alleles. Only minor modifications in the methods used for murine cells, all previously employed for other purposes, will be necessary to permit one of ordinary skill in the art to completely inhibit $ClqR_P$ expression in cultured human cells. One example of such a method of transgenic construction is described below. However, this example is not meant to be limiting as other transgenic constructions can be used which are commonly known to those in the art.

Insertion of the 1.2 kb Pol II-neomycin resistance cassette into an early exon of the $ClqR_P$ gene will disrupt the translational reading frame for $ClqR_P$ with the creation of an in-frame premature termination codon (PTC). Insertion of the PTC in an early exon will prevent translation of the C-terminus of $ClqR_P$ and will result in a complete loss of function. An alternate strategy is to target the very first exon eliminating the start-site for translation. N-terminal epitopes can also be used to determine whether a truncated protein is expressed from stabilized transcripts from the knockout allele.

Construction of a Targeting Vector

A large fragment of murine $ClqR_P$ cDNA is cloned, (~20 kb) murine (129/Sv) genomic clone spanning the five Epidermal Growth Factor-like domains, and characterized. A detailed restriction map of the clone and localizing intron-exon boundaries through a combination of the subcloning of relatively large (6–12 kb) restriction fragments into plasmid vector (pBlueprint II-SK) is determined, restriction analysis accompanied by Southern transfer and hybridization of radiolabeled oligonucleotide complementary to cDNA sequences, and direct sequencing of genomic subclones using cDNA primers can be done. Subsequently, a targeting vector is constructed using a (6–12 kb) genomic fragment which contains the exon of interest is subcloned into a suitable plasmid. Preferably, the exon is somewhat asymmetrically placed in the insert, with a minimum of ~2 kb of sequence at either end (Deng, et al., Mol Cell Biol 12: 3365–71, 1992). Genomic sequences that immediately flank the insert at the 5' and 3' ends are retained for use as probes in Southern analysis to confirm homologous recombination at a later time. The 1.2 kb Pol II-neomycin resistance expression cassette (Wang, et al., Nat Genet 11: 185–190, 1995) is inserted into the exon of interest using a suitable restriction site. The PGKtk expression cassette is added distal to the long arm of homology to enrich for homologous recombinants by FIAU selection (Li, et al., Cell 69: 915–26, 1992) (Andrikopoulos, et al., Nat Genet 9: 31–36 1995). The resultant construct is linearized and band-purified by $CsCl_2$ ultracentrifugation (Wang, et al., Nat Genet 1–1:185–190, 1995).

Additionally, recent advances in the efficiency of targeted gene delivery in cultured somatic cells can be used by one of ordinary skill in the art. Briefly, promoterless cDNAs that encode antibiotic resistance factors are used in targeting vectors such that expression can be driven by the promoter of the targeted allele upon homologous recombination. Enrichment ratios (homologous recombinants vs. random insertions) of up to 5,000 to 10,000-fold can be achieved compared to conventional methods (Hanson, et al., Mol Cell Biol 15: 45–51, 1995), thus efficiently inactivating both alleles by sequential gene targeting using two targeting vectors that contain different selectable genes.

Generation of Targeted Mice

Pluripotent J1 ES cells derived from the inner cell mass of 129/Sv blastocysts are cultured under standard conditions (Li, et al., Cell 69: 915–26, 1992). Approximately $1 \times 10^7$ cells are transfected with 10–20 µg of linearized construct by electroporation at 230 mV, 500 µF using a Bio-Rad Gene Pulser and are replated on a feeder layer of γ-irradiated G418-resistant primary mouse embryonic fibroblasts in Delbecco's modified Eagle's media supplemented with 5% FBS, 0.1 mM non-essential amino acids, 0.1 mM βME and 1000 U/ml leukemia inhibitory factor (Li, et al., Cell 69: 915–26, 1992). Selection with G418 and FIAU commences 24 hours after plating and is maintained for seven to ten days. An aliquot of each resistant colony (~90%) is frozen for later use and the remainder are replated and grown to confluence for DNA extraction. Identification of recombinant clones is accomplished by Southern analysis and facilitated by a single EcoR1 site in the Neo cassette and the probes that flank the homologous sequences are used for gene targeting as above. The 5'-flanking probe is used to detect a restriction fragment unique to the targeted allele. DNA from all positive clones are subsequently screened with the 3' probe to confirm bonafide homologous recombination (Wang, et al., Nat Genet 11: 185–190, 1995). Northern analysis are performed on RNA extracted from +/+ and ±colonies. By observing the size and abundance of hybridizing species of $ClqR_P$ RNA one of ordinary skill in the art can learn early valuable information regarding the influence of the haplo-insufficiency state for $ClqR_P$ upon the efficiency of the $ClqR_P$ expression of mRNA. In addition, the transcription rate and transcript stability can be determined using nuclear run-on analysis and Northern or RNase-protection analysis of RNA extracted at various intervals after the addition of actinomycin D (5 µg/ml) to inhibit new transcription (Urlaub, et al., Mol Cell Biol 9: 2868–80, 1989; Cheng et al., Mol Cell Biol 13: 1892–902, 1993). These parameters can be determined on an allele-specific basis by observing differences in transcript size or by using fusion probes which contain both $ClqR_P$ and Neo sequences.

Approximately 15 cells from each targeted ES cell clone are microinjected into each C57B1/6J blastocysts (~15) collected at 3.5 days post coitus. Chimeric offspring are identified by agouti (ES-derived) coat color. Male chimeras are bred with C57B1/6J females. Homozygotes for the targeted allele are be generated by the breeding of heterozygotes. The genotype of all mice are determined by Southern analysis or a PCR-based assay.

Characterization of Resultant Mice

The genetic complement of all initial mice are composed solely of the genomes of two well characterized inbred stains. Therefore, the murine genomes carry no deleterious recessive nonsense alleles other than the targeted $ClqR_P$ allele. Litter size, sex ratio, and genotyping of all newborn mice are used to monitor embryonic lethality. Mice of all 3 genotypes (+/+, ±and −/−) are examined carefully over time for any phenotypic differences including birth weight, growth, activity, and congenital or acquired anomalies. Non-viable mice undergo autopsy.

Molecular analysis of mice of all three genotypes are performed. First, the character and steady state level of $ClqR_P$ transcripts are determined by Northern analysis and RNase protection. Second, the level and distribution of reactive protein are determined by Western analysis and immunohistochemistry. Experiments can be performed to determine the allele-specific $ClqR_P$ transcription rates and transcript stabilities. A simultaneous analysis is performed on total, nuclear, and cytoplasmic RNAs (Daar, et al., Mol Cell Biol 8: 802–13, 1988). Gene dosage effects on $ClqR_P$ expression will be observed to determine the degree of reduction of $ClqR_P$ protein expression on hetereozygote cells ($ClqR_P^\pm$) compared with wild type. Finally, fetal fibroblast cultures are established and transfected with a construct expressing wild-type $ClqR_P$ to determine whether reconstitution with $ClqR_P$ can rescue an abnormal phenotype. Additionally, the functional consequences of $ClqR_P$ loss of expression ($ClqR_P^\pm$) to more clearly define the role of $ClqR_P$ in host defense against infection in vivo. To assess the effect of ClqR$_P$ deficiency on host defense, mice are challenged with intraperioteneal injection of virulent *Escherichia coli* (O18:K1:H7) (Cross et al., J. Exp. Med. 169, 2021 (1989); Lowrance et al., J. Exp. Med., 180, 1693 (1994)). ClqR$_P$ deficient mice are monitored to establish dose response mortality over time compared to wild-type and heterozygous (ClqR$_P^\pm$) littermates. Cellular infiltrate and bacterial colony counts are established to determine if the influx of other immune system cellular components (e.g., Polymorphonuclear leucocytes (PMN)) are impaired or enhanced. Quantitation of bacterial colony-forming units reveal when and if a defect in the control of bacterial growth is apparent after challenge.

Outcrossing of homozygous null (−/−) mice and further experimentation: To determine the phenotypic consequence of loss of the ClqR$_P$ enhancement of phagocytic function in different genetic backgrounds. The results can be compared to the tissue-specific expression pattern of ClqR$_P$ to determine whether the level of ClqR$_P$ is a limiting factor in the determination of tissue-specific components of the classical complement pathway of the immune system efficiency. Mice of all genotypes are analyzed, and the genotype-specific results can be compared.

If homozygosity for the targeted allele is incompatible with embryonic development, but heterozygosity is not associated with a phenotype, it is possible to generate dominant-negative or relative loss-of-function alleles. The size and character of such mutations would be influenced by expression studies using mammalian cells. The process of generating subtle (e.g. missense) mutations in the genome of ES-cells is well described and quite effective (Stacey, et al., *Mol Cell Biol* 14: 1009–16, 1994). Briefly, a targeting vector is first used to replace a defined region of the target gene in HPRT-deficient ES cells with an HPRT minigene. After selection for the HPRT+phenotype, a second round of targeting is used to replace the HPRT minigene with a desired DNA fragment that harbors a site-specified mutation. Enrichment for homologous recombinants is achieved by selection for reversion to the HPRT phenotype. Mice heterozygous for a dominant-negative mutation or homozygous for a relative loss-of-function mutation may have sufficient impairment of ClqR$_P$ efficiency to show a phenotype yet be viable. All potential mutations can be assessed in for their relative impact on host response to pathogenic challenge, immunocomplex clearance and kinetics of removal of cellular debris, and a select few can be used in transgenic experimentation.

Additionally, if homozygosity for the targeted ClqR$_P$ allele is incompatible with embryonic development, one of ordinary skill in the art can apply inducible gene targeting under the control of the CrelloxP recombination system of bacteriophage P1 (Sauer, et al., *Proc Natl Acad Sci USA* 85: 5166–70, 1988). The Cre recombinase directs site-specific recombination between two short recognition sequences (loxP) without additional co-factors. Cre recognizes the loxP sites and nicks them on opposite strands, leaving behind a single loxP site after recombination. This process deletes or inverts the intervening ("floxed") DNA sequence when the loxP sites are placed in a head-to-tail or head-to-head orientation, respectively. In vivo gene inactivation can be restricted to a specific development stage or tissue by crossing a mouse strain harboring a floxed allele to a transgenic strain of activation (Gu, et al., *Science* 265: 103–6, 1994; Kuhn, et al., *Science* 269: 1427–1429, 1995). Alternatively, an inducible promoter can be used to drive Cre expression. First, an exon or region of ClqR$_P$ would be flanked by two loxP sites using gene targeting methods described above. A resistance-conferring gene is included between the loxP sites but outside of the coding region for ClqR$_P$ to allow for positive selection of recombinant clones. Resulting mice are bred to homozygosity for this targeted, albeit functionally intact, allele. Resulting homozygotes are bred to a transgenic strain that expresses Cre under the control of a promoter with desirable characteristics. By bypassing certain critical developmental stages or tissues, one of ordinary skill in the art can create a viable and useful model of ClqR$_P$ deficiency despite the inherent essential nature of the gene product. The choice of the promoter for Cre expression can be an interferon-inducible promoter of the mouse Mx1 gene (Kuhn, et al, *Science* 269: 1427–1429, 1995).

The present invention may ameliorate mutations in ClqR$_P$ genes found in sites of pathogenic invasion, wounds, abrasions, epithelial intrusion, cellular debris or inflammation. Because the presence of mutant ClqR$_P$ polypeptide may correlate with vasculitis or sepsis, the ClqR$_P$ nucleic acid may find use in gene therapy to enhance phagocytosis for the treatment of diseases in which rapid clearance and/or inactivation of detrimental substances is required. In preferred therapies, the ClqR$_P$ regulating gene product is preferentially expressed in those cells where enhanced phagocytosis is required. Alternatively, therapy can be provided by administration of a peptidomimetic or other composition which mimics the biological activity of wild-type ClqR$_P$ polypeptides or which modifies the defect, such as a conformational defect, in a mutant ClqR$_P$ polypeptide to thereby restore the wild-type biological activity to the mutant polypeptide. Additionally, the ClqR$_P$ sequences taught herein can be used to effect the levels of various cytokines in a patient.

A preferred method of gene therapy is direct gene transfer, i.e., local application of a formulation containing the ClqR$_P$ polypeptide-encoding nucleic acid into an afflicted site or other region. A variety of well known vectors can be used to deliver the ClqR$_P$ gene to targeted cells in a location like an endothelial lining, including but not limited to adenoviral vectors, adeno-associated vectors or formulations targeting endothelial cells. In addition, naked DNA, liposome formulations delivery methods, or other novel formulations developed to deliver the ClqR$_P$ gene to target cells are also preferred.

For any of the above approaches, the therapeutic ClqR$_P$ polynucleotide construct can be applied to the site where enhanced phagocytosis is desirable (e.g., by injection), but the ClqR$_P$ formulation may also be applied to tissue in the vicinity of the needed phagocytosis event, to a blood vessel supplying the cells where phagocytosis is desirable or even systemically.

In the ClqR$_P$ gene delivery formulation of the instant invention, polynucleotide expression is directed from any suitable promoter (e.g., the human cytomegalovirus, simian virus 40, actin or adenovirus constitutive promoters; or the cytokine or metalloprotease promoters for activated synoviocyte specific expression). Furthermore, ClqR$_P$ polynucleotide production may be regulated by any desired mammalian regulatory element. For example, if desired, enhancers known to direct preferential gene expression in fibroblasts or macrophages may be used to direct ClqR$_P$ gene expression. Such enhancers include, without limitation, those enhancers which are characterized as tissue or cell specific in their expression.

Alternatively, if a ClqR$_P$-gene regulating genomic clone is utilized as a therapeutic construct, expression is regulated by its cognate regulatory sequences or, if desired, by regulatory sequences derived from a heterologous source, e.g., any of the promoters or regulatory elements described above.

Less preferably, gene therapy is accomplished by direct administration of the ClqR$_P$-regulating gene mRNA to a cell either in vitro, ex vivo, or in vivo. This mRNA may be produced and isolated by any standard technique, but is most readily produced by in vitro transcription using a cDNA under the control of a high efficiency promoter (e.g., the T7 promoter). Administration of mRNA to accumulated cells is carried out by any of the methods for direct nucleic acid administration described above.

Ideally, the production of the ClqR$_P$ protein by any gene therapy approach described herein results in a cellular level of the ClqR$_P$ polypeptide that is at least functionally equivalent to the normal, cellular level in a normal individual. Treatment by any gene therapy approach described herein may also be combined with more traditional therapies.

Another therapeutic approach included within the invention involves direct administration of recombinant ClqR$_P$ protein by any conventional recombinant protein administration techniques, to the site of infaccumulaat the site where pathogenic cells accumulate (for example, by injection), or administered systemically. The ClqR$_P$ protein may also be targeted to specific cells or receptors by any of the methods described herein to target ClqR$_P$ nucleic formulations. The actual dosage of protein depends on a number of factors, including the size and health of an organism, however one of one of ordinary skill in the art can use the following teachings describing the methods and techniques for determining clinical dosages (Spilker B., *Guide to Clinical Studies and Developing Protocols*, Raven Press Books, Ltd., New York, 1984, pp. 7–13, 54–60; Spilker B., *Guide to Clinical Trials*, Raven Press, Ltd., New York, 1991, pp. 93–101; Craig C., and R. Stitzel, eds., *Modern Pharmacology*, 2d ed., Little, Brown and Co., Boston, 1986, pp. 127–33; T. Speight, ed., *Avery's Drug Treatment: Principles and Practice of Clinical Pharmacology and Therapeutics*, 3d ed., Williams and Wilkins, Baltimore, 1987, pp. 50–56; R. Tallarida, R. Raffa and P. McGonigle, *Principles in General Pharmacology*, Springer-Verlag, New York, 1988, pp. 18–20) to determine the appropriate dosage to use; but, generally, between 0.1 mg and 100 mg inclusive are administered per day to an adult in any pharmaceutically-acceptable carrier.

In one embodiment, the invention provides a method of treating a patient having or at risk of having early stage infection when little or no antibody is present to attack antigenic or pathogenic agents or under conditions in which an individual is immuno-compromised as a result of genetic deficiency, disease or clinical treatment or the condition has an etiology associated with a defective phagocytosis-regulating gene or polypeptide, deficient ClqR$_P$ or level thereof, or an inability to overcome infection (e.g., such as a post-operative patient), the method comprising administering to the patient a therapeutically effective amount of a formulation or composition which modulates the expression of the ClqR$_P$ gene or polypeptide or triggers functional activation of the ClqR$_P$ receptor such that the state of the patient is ameliorated. Furthermore, since it has been demonstrated that Clq enhances macrophage mediated tumor cell killing in vitro, one of ordinary skill in the art would recognize that modulation of ClqR$_P$ (e.g., through upregulation of ClqR$_P$ by administration of a ClqR$_P$ formulation) could become part of a treatment for various forms of cancer.

Therapeutic applications also include utilizing a selective survival technique taking advantage of those cells specifically expressing the wild-type protein, e.g., ClqR$_P$. Such treatment kills or inactivates the cell that contains a defective ClqR$_P$ gene, while leaving cells containing the wild type or normal ClqR$_P$ gene/polypeptide unharmed. Several approaches for selective killing include but are not limited to: 1) infection with a viral vector to induce expression of the endogenous, normal ClqR$_P$ gene,; 2) contact a cell having a mutant ClqR$_P$ protein with an agent that specifically binds to the mutant and not the wild-type protein; and 3) contact a cell having a mutant ClqR$_P$ protein with a first agent that protects the wild-type ClqR$_P$ and then a second agent that is toxic to a mutant ClqR$_P$.

EXAMPLES

The following examples are intended to illustrate but not admitted to limit the invention in any manner, shape, or form (either explicitly or implicitly). While they are typical of those that might be used, other procedures, methodologies, or techniques known to those skilled in the art may be used alternatively.

MATERIALS AND METHODS

Reagents and Cell Culture

The ImmunoPure IgM Purification Kit, ReactiGel (6×) Support and NP-40 were purchased from the Pierce Chemical Co., Rockford, Ill. Protein A-Sepharose and CNBr-Sepharose were from Pharmacia Biotech Inc. (Piscataway, N.J.). TPCK-trypsin was purchased from Worthington (Freehold, N.J.). The RPMI 1640 medium, Dulbecco's modified eagle medium, SuperScript Preamplification System for First Strand cDNA Synthesis Kit, DNAZOL Reagent, RadPrime DNA Labeling System, herring sperm DNA and 0.24–9.5 Kb RNA Ladder were obtained from GIBCO BRL (Grand Island, N.Y.). Except where noted otherwise, all other reagents were purchased in the highest quality from Sigma Chemical Company (St. Louis, Mo.). The human histiocytic cell line, U937, was grown in suspension at 37° C., in RPMI 1640 medium containing 10% supplemented bovine calf serum (Hyclone, Logan, UT) and 10 mM HEPES, pH 7.4. The human acute lymphoblastic leukemia cell line, CEM, was grown in Dulbecco's modified eagle medium supplemented with 10% FCS (Hyclone). RPMI 1640 medium was purchased from Gibco (Long Island, N.Y.). HL-1 medium (serum free) was purchased from Ventrex Laboratories (Portland, Me.). Fetal calf serum (FCS) was purchased from Hyclone (Logan, Utah). L-glutamine and gentamicin were obtained from M.A. Bioproducts (Walkersville, Md.). The human serum albumin (HSA) used for the elutriation buffer obtained from the American Red Cross was prepared by Baxter Healthcare Corporation (Glendale, Calif.). Human recombinant γ-interferon was a gift from Dr. Krishna Tewari (UC, Irvine and ICGEB, New Delhi, India).

Antibodies

The R3 mAb and 710 polyclonal antiserum were generated by immunization with Clq-CLF binding proteins isolated from U937 cell extracts as previously described (Guan et al. *J. Immunol.* 152: 4005, 1994). Polyclonal antiserum QRl was generated by immunization of a rabbit with the 126,000 M$_r$ ClqR$_P$ band extracted from agarose gels after separation by electrophoresis using the ProSieve Gel System (FMC BioProducts, Rockland, Ma.) according to manufacturer's instructions. The anti-peptide polyclonal antiserum was generated by immunization with a mixture of two peptides, VGGGEDTPYSN (SEQ ID NO: 11) and VGGGEDTPYSNK (SEQ ID NO: 12) (to allow conjugation at the C-terminal amino acids), conjugated to keyhole limpet hemocyanin using glutaraldehyde as the crosslinker as described (Current Protocols in Immunology). Purified R3 IgM was obtained from ascites fluid using the ImmunoPure IgM Purification Kit according to manufacturer's instructions. 710 IgG was purified by affinity chromatography using protein A-Sepharose as described (Andrew and Titus Curr. Prot. Immun. Wiley Interscience, N.Y., 2.7.4., 1991).

Protein Isolation and Amino Acid Sequencing

Purified 710 IgG was coupled to CNBr-activated Sepharose 4B and purified R3 IgM was coupled to Reacti-Gel (6×) according to manufacturer's directions. For a single preparation, approximately $6 \times 10^8$ U937 cells were washed once in ice cold RPMI 1640, then once in ice cold PBS, pH 7.4. The pelleted cells were resuspended to a concentration of $10^8$ cells/mL in extraction buffer (10 mM triethanolamine, pH 7.4, 1 mM $CaCl_2$, 1 mM $MgCl_2$, 0.15M NaCl, 0.3% NP-40, 1 µg/mL pepstatin, 5 µg/mL leupeptin, 1 µg/mL aprotinin and 1 mM phenylmethylsulfonyl fluoride (PMSF)). After a 1 hr incubation on ice with occasional agitation, the cell extract was centrifuged at 4° C. at 12,000 g for 10 min to pellet insoluble material. The extract was pre-cleared by incubation for 1 hr on ice with 40% (v/v) packed Sepharose CL-4B. The Sepharose was removed, the lysate diluted five fold with 20 mM Tris pH 7.4, 0.15M resulting in peptide sequences 112 and 115 (Table 1). Gel slices containing receptor isolated by R3 affinity chromatography were digested in situ using TPCK-trypsin using the procedure of (Ward et al., J. Chromatog 519: 1990). After isolation of the peptide fragments using a $C_4$ reverse phase column (Vydac, Hesperia, Calif.), the peptide-containing peaks were subjected to protein sequencing by the Edman degradation method carried out on a Hewlett-Packard Protein Sequencing System, model G1005A, with an on-line analyzer of the amino acid derivatives. The resulting peptide sequences are labeled in Table 1 as beginning with the letters AH. Other preparations of the protein after SDS-PAGE were electrophoretically transferred to nitrocellulose as described by Towbin et al. (Towbin et al., Proc. Nat. Acad. Sci. 76: 4350, 1979) for 2–3 h, with the addition of 0.02% SDS to the transfer buffer. The membrane was then stained for 10 min in 0.5% Ponceau S in 1% acetic acid, then destained with 0.1 mM acetic acid. Both the 126,000 $M_r$ and 90,000 $M_r$ bands were cut from the nitrocellulose subjected to either N-terminal sequencing or internal peptide sequencing after endo-Lys-C digestion and separation of peptides by HPLC ("BB" peptides in Table 1).

TABLE 1

$C1qR_p$ Peptides Determined by Amino Acid Sequencing

|  | Peptide ID | Sequence[a] |  |
| --- | --- | --- | --- |
| Endo Lys-C Digestion | 112 | FWIGLQREK | (SEQ ID NO: 13) |
|  | 115[b] | GFSXVGGGEDTPYSNXHK | (SEQ ID NO: 14) |
| N-terminus | BBN | VGADTEAVVXXGTATYRIHXKL | (SEQ ID NO: 15) |
| Endo Lys-C Digestion | BB3 | XGATVPQAATASPTGGPEGV | (SEQ ID NO: 16) |
|  | BB7 | ATPTTSRPSL | (SEQ ID NO: 17) |
|  | BB10[b] | GFSWVGGGEDTPXSNXHK | (SEQ ID NO: 18) |
|  | BB14 | APDVFDWGSXGPLXVY | (SEQ ID NO: 19) |
|  | BB17 | AMXXPLALGGPGQVTYTTPFQXT | (SEQ ID NO: 20) |
| Trypsin Digestion | AH28 | KPQNAADSYSWVPER | (SEQ ID NO: 21) |
|  | AH31 | VLAQLLR | (SEQ ID NO: 22) |
|  | AH37 | FWIGLQR | (SEQ ID NO: 23) |
|  | AH39[b] | GFSWVGGGEDTPYSNWHK | (SEQ ID NO: 24) |
|  | AH45 | TTPFQTTSSSLEAVPFASAANVAAGEG | (SEQ ID NO: 25) |
|  | AHA[c] | YGXNFXNG | (SEQ ID NO: 26) |
|  | AHBc | PQGYQLDXXQ | (SEQ ID NO: 27) |
|  | AHCc | MLAP | (SEQ ID NO: 28) |

[a]Discrepancies from deduced amino acid sequence are indicated as bold residues.
[b]Peptide sequence (underlined) used to generate anti-peptide antiserum.
[c]New peptide sequences identified from sequencing data of the peptide mixtures.

NaCl, 1 mM PMSF to dilute the NP-40 to a final concentration of 0.05%, then applied to the antibody column at 4° C. After washing with 10 column volumes of 20 mM Tris, pH 7.4, 0.5M NaCl, 0.05% NP-40, 1 mM PMSF, the bound antigen was eluted with 0.1M glycine, pH 2.4, 0.5M NaCl, 0.5% NP-40, 1 mM PMSF. $ClqR_P$ containing fractions were pooled and concentrated by ultrafiltration using Centricon 30 concentrators (Amicon, Inc., Beverly, Ma.). The protein was then precipitated overnight on ice using trichloroacetic acid at a concentration of 10%, and the precipitate washed with ice cold acetone. The pellet was resuspended in 20 µL Laemmli loading buffer (Laemmli, Nature 227: 680, 1970), boiled for 5 min, and subjected to SDS-PAGE (7.5% acrylamide) under reducing conditions. In some instances, the gels were stained directly with Coomassie blue, and the 126,000 $M_r$ band was excised from the gel. Gel slices containing protein isolated from the 710 column was sent to the W. M. Keck Foundation Biotechnology Resource Laboratory at Yale University for endoproteinase Lys-C (endo-Lys-C) digestion and subsequent amino acid sequencing, Clq was isolated from plasma-derived human serum by the method of Tenner et al. (Tenner, et al., J. Immunol., 127:648, 1981) and modified as described in Young, et al., J. Immunol., 146:3356, 1991. The preparations used were fully active as determined by hemolytic titration and homogeneous as assessed by sodium dodecyl sulfate polyacrylamide gel electrophoresis. Protein concentration was determined using an extinction coefficient ($E^{1\%}$) at 280 nm of 6.82 for Clq. All proteins were stored at −70° C. Purified human fibronectin was generously provided by Drs. Sheila Huff and Kenneth Ingham (American Red Cross Holland Laboratory, Rockville, Md.), and human SPA isolated from alveolar proteinosis patients was a generous gift from Dr. Jo Rae Wright, Duke University, Durham, N.C.

PCR and Library Screening

Generation of PCR3

To obtain the 5' region of the cDNA, the 5' RACE System for Rapid Amplification of cDNA Ends was used according to manufacturer's instructions. The gene-specific primer 1 (GSP1) used to generate the cDNA from 1.75 µg of U937 total RNA was 5'-TTGGCCGCAGAGGCAAAGGGCA-3' (SEQ ID NO: 29). The primary PCR reaction was done with the supplied 5' RACE Abridged Anchor Primer and a nested primer, GSP2, of the SEQ ID NO: 30, 5'-CAAGGAGGAACTGGTGGTCTGG-3'. The reaction products from this primary PCR was used as the template for a final PCR reaction using the supplied Abridged Universal Amplification Primer and another nested primer, GSP3, of the SEQ ID NO: 31: 5'-TGGGCCTCGGCAGCGCTCAGCT-3'. The resulting 297 bp PCR product was cloned into the pGEM-T vector and sequenced.

A trypsin cleavage in the protein after a tyrosine residue allowed for the overlap of peptides BB17 and AH45, which includes the sequence, SEQ ID NO: 6: GGPGQVTYT-TPFQTTSSSLEAVPFASAANVACGE. Based on this sequence, two degenerate primers were synthesized and used for RT-PCR using cDNA generated with the Super-Script Preamplification System for First Strand cDNA Synthesis Kit according to manufacturer's instructions from mRNA isolated from U937 cells as template. The forward oligonucleotide was SEQ ID NO: 32: 5'-GG(agct)GG(agct)CC(agct)GG(agct)CA(ag)GT(agct)AC-3' and the reverse was SEQ ID NO: 33: 5'-TC(agct)CC(agct)GC(agct)GC(agct)AC(ag)TT(agct)GC-3'. The PCR product of 101 bp was isolated on a 12% polyacrylamide gel (Sambrook et al., 1989), cloned into the pGEM-T vector (Promega Corporation, Madison, Wis.) and sequenced using the Sequenase Quick-Denature Plasmid Sequencing Kit (USB, Cleveland, Ohio) to confirm that it encoded the expected peptide. A specific primer based on this PCR product, SEQ ID NO: 30: 5'-CAAGGAGGAACTGGTGGTCTGG-3', and a degenerate primer based on the sequenced amino terminus starting at amino acid 2, SEQ ID NO: 33: 5'-GGIGCIGA(tc)ACIGA(ag)GC-3', were used to amplify by RT-PCR the cDNA corresponding to the amino terminus of the protein from U937 mRNA. This 570 bp PCR product was also cloned into the pGEM-T vector and sequenced, and then was used to screen a λgt11 U937 cDNA library (Clontech, Palo Alto, Calif.), using conventional techniques. The 1458 bp Eco RI insert from a positive phage (clone 15) was cloned into pBluescriptII-KS(+) (Stratagene, La Jolla, Calif.), sequenced, then used to rescreen the U937 λgt11 cDNA library. Four new positive phage were isolated and both ends of each insert was sequenced using the fmol DNA Sequencing System (Promega) to determine their position relative to clone 15. Clone 3, which contains a 1832 bp insert that extends the farthest downstream, was then cloned into pBluescriptII-KS(+) and sequenced in its entirety. Sequencing of the phage clone inserts 3 and 15 were done using the Erase-a-Base System (Promega) and the Sequenase Quick-Denature Plasmid Sequencing Kit to obtain unambiguous overlapping readings from both strands. Computer analysis of the sequencing data was done using the Lasergene DNASTAR for Windows software.

Sequence Analysis

The National Center of Biotechnology Information (NCBI) electronic mail server BLAST was used to search for homologous sequences in the non-redundant compilation of the protein databases. Motif searches were done using the Motifs program of the GCG computer package, Version 8 (Madison, Wis.) and the transmembrane domain was predicted using the TMpred program (Hoffmann and Stoffel, *J. Biol. Chem.*, 347:166, 1993).

Western Blot

After R3 affinity purified ClqR$_P$ was transferred to nitrocellulose (described above), the membrane was blocked with 3% nonfat dry milk in Tris-buffered saline, containing 0.05% Tween 20 (TBST). R139 and control IgG$_{2b}$ were diluted to 5 μg/mL and the rabbit antisera were diluted 1:1000 in the blocking buffer. Bound antibodies were detected using peroxidase-conjugated anti-mouse IgG or anti-rabbit IgG and the peroxidase was detected using 4-chloro-1-naphthol (Bio-Rad Laboratories, Hercules, Calif.).

Southern Blot Analysis

Human genomic DNA was isolated from whole blood using DNAZOL Reagent according to manufacturer's directions. For each digest, 10 μg of DNA was restricted with either Bam HI, Eco RI, Hind III or Pst I, then separated by electrophoresis on a 0.7% agarose gel in 0.5× TBE. The DNA was fractionated, transferred overnight in 10× SSPE to Maximum Strength Nytran (Schleicher and Schuell, Inc., Keene, N.H.), and immobilized using a Stratalinker UV Crosslinker (Stratagene). The clone 15 insert was used as the template to make a $^{32}$P labeled probe generated by the random priming method using the RadPrime DNA Labeling System. Hybridization of the probe was carried out for 16 hrs at 42° C. in 50% formamide, 6× SSPE, 5× Denhardt's reagent, 0.5% SDS and 0.5 mg/mL herring sperm DNA. Washing was done as follows: twice in 7× SSPE, 0.5% SDS for 15 min each at room temperature, twice in 1× SSPE, 0.1% SDS for 15 minutes each at 37° C., then finally once for 30 min at 55° C. in 0.1× SSPE, 0.5% SDS. The membrane was wrapped in plastic wrap and exposed to autoradiographic film for two days at −70° C.

Northern Blot Analysis

Messenger RNA was isolated from U937 and CEM cells using the Micro-FastTrack mRNA isolation kit (Invitrogen, San Diego, Calif.). One ug of each RNA was separated in each of two lanes on a denaturing 1% agarose gel containing formaldehyde. The RNA was transferred overnight in 20× SSPE to Maximum Strength Nytran, UV crosslinked to the membrane, then probed with the clone 15 insert as in the Southern blot. A 0.24–9.5 Kb RNA Ladder was used as a size marker. After washing twice in 6× SSPE, 0.1% SDS for 15 min each at room temperature, twice in 1× SSPE, 0.1% SDS for 15 min at 37° C. and once in 1× SSPE, 0.1% SDS for 30 min at 50° C., bound probe was detected by autoradiography for 3 days at room temperature.

Cells

Human peripheral blood monocytes were isolated by counterflow elutriation using a modification of the technique of Lionetti et al. (Lionetti et al., *Methods of Cell Separation*, Plenum Publishing Corp. New York, p. 141, 1980) as described (Bobak et al., *J. Immunol.*, 136:4604, 1986). Blood units were collected into CPDA1 at the UCI Medical Plaza, Irvine, Calif. Greater than 95% of the cells in each preparation were monocytes according to size analysis on a Coulter Channelyzer. Cells were cultured in RPMI 1640 supplemented with 10% FCS or in HL-1 medium. One-well Lab Tek chambers (Nunc, Naperville, Ill.) were coated with Clq, SPA or other control or test proteins (8–16 μg/mL) in coating buffer (0.1 M carbonate, pH 9.6), and incubated at 37° C. for 2.5 h. After washing chambers twice with PBS, monocytes (2 ml of $10^6$/ml) were added to chambers and cultured for various periods of time at 37° C. in 5% $CO_2$ air. Where indicated, LPS (100 ng/ml) or INFγ (100U–300U/ml) was added directly to the monocytes.

Phagocytosis Assay

Sheep erythrocytes (E) bearing either IgG anti sheep red blood cells (EA$_{IgG}$) or IgM anti sheep red blood cells and C4b (EA$_{C4b}$) were prepared as previously described (Bohnsack et al., *J. Exp. Med.* 161:912, 1985). Eight-well Lab Tek chambers were coated with varying concentrations of Clq, SPA, iron-saturated transferrin (Sigma) or HSA (Bobak et al., Eur. J. Immunol. 18:2001, 1988). Monocytes or macrophages ($6.25 \times 10^4$ cells/well) are added to each chamber, the cells centrifuged at 600 rpm (RT6000, Dupont Sorvall) for 3 min and subsequently placed at 37° C. in 5% $CO_2$ for times noted. Targets were then added (107/100 µl), the slides again subjected to centrifugation (600 rpm, 3 min), and incubated for 30 min at 37° C. After removing $EA_{IgG}$ or $EA_{C4b}$ not cell-associated by washing, non-ingested targets were removed by hypotonic lysis (Bobak et al., supra). After fixation in 1% glutaraldehyde and staining with Giemsa, phagocytosis was quantitated using light microscopy. The number of E-targets ingested per 100 effector cells was defined as the phagocytic index, whereas the percentage of effector cells ingesting at least one E-target was defined as the percent phagocytosis. Each experiment, performed on separate days with different donors, used duplicate sample wells per condition. Controls of unopsonized E were not ingested by monocytes or macrophages under any conditions.

RNase protection assay

At various culture times, total RNA was extracted from both adherent monocytes and nonadherent monocytes (recovered by centrifugation of cell supernatants), using the TRIzol™ reagent (GIBCO BRL, Grand Island, N.Y.) following manufacturer's direction. The ribonuclease protection assay (RPA) was performed exactly as described (Hobbs et al., J. ImmunoL 8: 3602 1993.). Briefly, 50 ng of EcoRI linearized template for each cytokine was used in an in vitro transcription reaction (Promega, Madison, Wis.) using $[\alpha-^{32}P]$-UTP (3000 $ClqR_P$/mmol, Amersham, Arlington Heights, Ill.) to generate the radiolabeled riboprobe template set, HL-14. The HL-14 template set was previously described (Rochford, et al., manuscripts submitted) and contains linearized templates specific for IL-6 (320 bases protected mRNA), IL-10 (294 bases), IL-1α (269 bases), TNF-β (220 bases), GM-CSF (208 bases), TGF-β1 (170 bases), IL-1α (149 bases), TNF-α (124 bases), and rpL32 (76 bases). Labeled antisense RNA was hybridized overnight with the total RNA. Yeast tRNA was added to each sample to bring the final RNA content to 5–10 µg. Unprotected (single stranded) RNA was then digested by addition of 2 µl RNase T1 (2000 U/µl, GIBCO BRL). In initial experiments 5 µl RNase A (100 µg/ml, Sigma) was also added, but was discontinued since no advantage was seen. Protected fragments were analyzed by electrophoresis in 5% acrylamide/8 M urea gels. Dried gels were placed on XAR film (FUJI Medical film) with intensifying screens, and were developed at –70° C. For signal quantitation, in some experiments dried gels were analyzed with the GS-250 Molecular Imager™ (Bio-Rad) and volume measurements of each protected band was determined.

ELISA

The levels of human IL-1β, IL-6, and TNF-α in culture supernatants were measured by using two-site sandwich ELISA. The TNF-α cytokine standard, rabbit anti-rh-TNF-α IgG, and rabbit HRP-anti-TNF-α IgG were a gift from Dr. Gale Granger (University of California, Irvine, Calif.), and the ELISA assay used was as described (Choi et al., Cell. Immunol. 1996.). Microtiter plates were coated with 100 µl of rabbit anti-rh-TNF-α IgG at 5 µg/ml in 0.05 M carbonate buffer, pH 9.6. After overnight incubation at 4° C., the plates were washed with PBS containing 0.2% Tween 20 (PBS-Tween). After washing, serial dilutions of the test supernatants and the TNF-α standard (in 1% BSA/PBS) were added (100 µl/well). Following overnight incubation, wells were washed 3 times with PBS-Tween and incubated with rabbit HRP-anti-TNF-α IgG at 2 µg/ml in 1% BSA/PBS for 1 h, 37° C. Finally, after washing, 100 µl of ABTS (1 mg/ml in 0.1 M Acetate buffer, pH 4.2 and 0.03% $H_2O_2$) was added to each well, and the change in $A_{405}$ was monitored using a thermoregulated (24° C.) Molecular Devices microplate reader. Comparison with log-log plots of absorbance vs standard cytokine concentration were used to calculate cytokine levels in supernatants. Alternatively, TNF-α was measured using an ELISA kit from PerSeptive Diagnostics.

The levels of IL-1β and IL-6 in culture supernatants was measured using commercially available test kits (R&D Systems, Minneapolis, Minn. and PerSeptive Diagnostics, Cambridge, Mass.).

EXAMPLE 1

PURIFICATION, CHARACTERIZATION, AND PEPTIDE SEQUENCING OF THE $ClqR_P$ RECEPTOR PROTEIN

To gain a further understanding of how $ClqR_P$ functions to enhance phagocytosis triggered by its known ligands, the structure of the receptor is required. Accordingly, the $ClqR_P$ receptor protein was isolated to obtain amino acid (aa) sequence data to design degenerate oligonucleotide probes and/or PCR primers.

Purified 710 or R3 antibodies were used to affinity purify $ClqR_P$ from NP-40 detergent extracts of U937 cells. The eluted material was concentrated by ultrafiltration, precipitated with trichloroacetic acid, then separated by SDS-PAGE under reducing conditions.

The mature protein migrates with an apparent molecular weight of 126,000. Two additional bands with apparent molecular weights of 90,000 and 60,000 were variably seen and are most likely breakdown fragments resulting from the purification procedure since both fragments are also reactive with anti-$ClqR_P$ antibodies. Additionally, the 90,000 $M_r$ fragment shares the identical N-terminus, as well as certain internal peptides as the mature protein.

The 126,000 $M_r$ receptor protein was excised from SDS-PAGE gels and subjected to either trypsin or endo-Lys-C digestion and subsequent peptide sequencing. In another approach, both the 126,000 $M_r$ and 90,000 $M_r$ proteins were transferred to nitrocellulose for N-terminal sequencing, as well as internal peptide sequencing following endo-Lys-C digestion. The sequenced peptides are summarized in Table 1. One sequence, FWIGLQREK, is found among other membrane receptors that are reported to modulate endocytosis, including the human and murine mannose macrophage receptor (Ezekowitz et al., J. Exp. Med. 172: 1785, 1990), chicken hepatic lectin (Drickarner et al. J. Biol. Chem. 261:6878, 1986) and the beta subunit of human fibronectin receptor (Argraves et al., J. Cell Biol, 105:1183, 1987). This finding is consistent with the fact that $ClqR_P$ plays a role in modulating monocyte phagocytosis.

EXAMPLE 2

CLONING OF THE $ClqR_P$ cDNA

A trypsin cleavage within the purified protein at the C-terminus of a tyrosine residue resulted in the peptide AH45 (Table 1). The beginning of this peptide overlaps the last seven amino acids of peptide BB17, resulting in a 44 amino acid sequence.

Degenerate oligonucleotide primers were used to amplify, by RT-PCR, a 101 bp cDNA fragment from U937 mRNA corresponding to 34 amino acids of the overlapping peptide sequences AH45 and BB17. Specific primers based on this 101 bp cDNA were used in combination with another degenerate primer corresponding to the amino terminus of the protein, starting at the second amino acid, to amplify a 570 bp cDNA of $ClqR_P$. This 570 bp fragment was used to screen a U937 λgt11 cDNA library. A phage was identified (clone No. 15) which contained a 1458 bp insert that overlapped the 570 bp PCR product by 165 bp.

The insert from clone No. 15 was used to rescreen the U937 λgt11 cDNA library and four additional, distinct phage inserts were identified. Clone No. 3 contained a 1832 bp insert that overlapped clone No. 15 by 449 bp. To obtain the 5' end of the cDNA, specific primers based on sequences derived from the 570 bp PCR product were used in 5' RACE-PCR reaction to amplify a 297 bp product which overlaps the 570 bp cDNA by 83 bp.

EXAMPLE 3

SEQUENCING THE $ClqR_P$ RECEPTOR NUCLEOTIDE CLONES

The PCR products and clones Nos. 15 and 3 were sequenced in their entirety on both strands and a 3460 bp of total cDNA was translated. The open reading frame of the cDNA encodes a 652 amino acid protein, which, excluding the 21 amino acid signal peptide (based on the N-terminal sequence) has a predicted molecular weight of 66,495 Daltons and a pI of 5.24. The amino terminal sequence starting at the second amino acid, as well as all ten of the sequenced internal peptides are found within the predicted amino acid sequence, indicating that this cDNA corresponds to the isolated $ClqR_P$ protein.

The stop codon for the protein is located 54 bp downstream of the most C-terminal peptide determined by amino acid sequencing. The nucleotide sequence has been configured by re-sequencing both strands of the cDNA three separate times.

EXAMPLE 4

SEQUENCE ANALYSIS OF $ClqR_P$

Homology searches of the protein and nucleotide data bases indicate that $ClqR_P$ is a novel protein whose structural domains are shown in FIG. 4. There is a single C-type carbohydrate recognition domain at the amino terminus, containing seven of the 18 nearly invariant residues (Drickamer *J. Biol. Chem.* 263:9557, 1988), including the four cysteine residues that are involved in disulfide bonds within the domain. The protein also contains a set of five epidermal growth factor (EGF)-like domains, the last three of which contain an asparagine hydroxylation motif consistent with calcium binding EGF domains (Rees et al., *Embo J.* 1: 2053, 1988).

$ClqR_P$ shows homology to the other diverse, non-related, extracellular proteins due to their EGF domains, including fibrillin, thrombomodulin, and fibulin.

There is a single putative N-linked glycosylation site at residue N325 (FIG. 3, italics). At the carboxy terminus, there is a single 25 amino acid transmembrane domain (FIG. 3, double underline), and finally a short, 47 amino acid cytoplasmic tail. Within the cytoplasmic tail, there is a tyrosine residue at position Y644 that is part of a consensus motif which is recognized by tyrosine kinases (Patschinsky et al., *Proc. Natl. Acad. Sci.* 79:973, 1982). Once the cDNA was translated and the primary amino acid sequence known, amino acid sequence data of HPLC peaks containing peptide mixtures derived from the trypsin digest of $ClqR_P$ were reexamined. In addition to re-identifying 11 of the peptides previously sequenced, three new peptide sequences were found (Table 1), further confirming that the cloned cDNA encodes the isolated, monoclonal antibody reactive protein.

EXAMPLE 5

WESTERN BLOT ANALYSIS OF $ClqR_P$

A synthetic peptide (SEQ ID NO: 11, VGGGEDTPYSN), based on the internal peptide sequence encoded in the cloned $ClqR_P$ cDNA, was synthesized by three independent facilities using three different protocols and subsequently used to generate a rabbit polyclonal $ClqR_P$ anti-peptide antiserum. Using western blot analysis on purified $ClqR_P$ transferred to nitrocellulose, the anti-peptide $ClqR_P$ antibody reacted with the 126,000 $M_r$ $ClqR_P$ receptor in both its reduced and nonreduced forms. The anti-peptide $ClqR_P$ antibodies also recognized the 90,000 $M_r$ $ClqR_P$ breakdown fragment, but not the smaller 60,000 $M_r$ $ClqR_P$ fragment, indicating that the 60,000 $M_r$ $ClqR_P$ fragment does not contain the N-terminus of the $ClqR_P$ protein. The fact that the anti-peptide antiserum reacted with two forms of the $ClqR_P$ receptor (the 126,000 $M_r$ full length and its 90,000 $M_r$ breakdown fragment) in both reduced as well as nonreduced mobility shifted forms, and that the synthetic peptide encoded by the cloned $ClqR_P$ cDNA (SEQ ID NO: 11, VGGGEDTPYSN), was sequenced by three separate facilities using different protocols to generate the peptide fragments, strongly suggests that the cloned $ClqR_P$ cDNA encodes the native $ClqR_P$ protein.

EXAMPLE 6

ANALYSIS OF GENOMIC $ClqR_P$ DNA BY SOUTHERN BLOT

To characterize the genomic organization and expression of $ClqR_P$, Southern blotting was done using a probe based on the insert of clone No. 15. Clone No. 15 corresponds to 486 amino acids of the coding region, beginning at position P136.

Human genomic DNA, isolated from whole blood, was digested with restriction enzymes and separated by agarose gel electrophoresis. The DNA was transferred to a nylon membrane and hybridized to a probe generated by the random priming method. A single band hybridized in three of the four digests indicating that the gene encoding for $ClqR_P$ is present as a single copy in the human genome. Two bands were visible in digests using Eco RI. These two band are interpreted as being present as a result of the presence of restriction site(s) within a $ClqR_P$ intron, since no such Eco RI restriction enzyme sites are present in the cDNA insert of clone No. 15.

EXAMPLE 7

ANALYSIS OF $ClqR_P$ mRNA BY NORTHERN BLOT

To determine the size of the mRNA of $ClqR_P$, mRNA was isolated from U937 cells, separated by agarose gel electrophoresis and transferred to a nylon membrane. Using a probe generated as in the Southern blot of Example 6, the mRNA for $ClqR_P$ was found to be a single species that was 6.7 Kb in size.

In contrast, a $ClqR_P$ probe did not hybridize to mRNA isolated from CEM cells which are of a different cell type than U937 cells. The specificity of $ClqR_P$ mRNA to a particular cell type is consistent with our previous work demonstrating that while the $ClqR_P$ protein is expressed on the surface of U937 cells it is not expressed on the surface of CEM cells (Guan et al. *J. Immunol.* 152:4005, 1994).

EXAMPLE 8

$ClqR_P$ DOES NOT TRIGGER CYTOKINE mRNA EXPRESSION

To determine the efficacy of using $ClqR_P$ to bolster the complement component of the immune system we attempted to determine if $ClqR_P$ also stimulated an inflammatory response since co-stimulation of an inflammatory response with stimulation of phagocytosis would not be desirable. Therefore, we performed an analysis of the effect of $ClqR_P$ interaction with monocytes on the subsequent mRNA expression of selected cytokines in cells cultured in HL-1 media.

HL-1 media is a defined low protein synthetic medium, chosen to exclude possible effects of external proteins on cytokine synthesis and to mimic more closely the serum-free assay conditions under which $ClqR_P$ enhances phagocytosis of opsonized targets.

Cytokine mRNA expression was examined using an RNase protection assay after incubation of monocytes with no stimulus or in $ClqR_P$-coated wells, in the absence or presence of LPS for 1 h (a time at which $ClqR_P$-enhanced phagocytosis is evident) and for 18 h (to assess the long term effect of $ClqR_P$). LPS was added to the media as a positive control since it was well established that LPS stimulates monocytes to synthesize TNF-$\alpha$, IL-1$\beta$, and IL-6 which are known to promote inflammation.

Control cells, cultured in uncoated wells, expressed substantial levels of mRNA for the cytokines TNF-$\alpha$, IL-1$\beta$ and TGF-$\beta$1 at both 1 h and 18 h of culture. IL-6 and IL-1$\alpha$ mRNA expression, while nearly undetectable at 1 h, was quite prominent by 18 h of culture. Exposure of monocytes to LPS increased IL-1$\alpha$, IL-1$\beta$, IL-6 and TNF-$\alpha$ mRNA levels relative to untreated cells at 1 h and significantly (3–10 fold relative to untreated controls) after 18 h of culture.

In contrast, at 1 h $ClqR_P$ had a slight, but consistent, suppressive effect on the levels of detectable cytokine mRNA relative to the basal level of cytokine mRNA synthesis by cells in HL-1 media alone. After 18 h of incubation, cytokine MRNA levels in cells exposed to $ClqR_P$ were greatly reduced when compared both to the 1 h time point and compared to the control cells at 18 h. The IL-6 mRNA level was 20-fold lower and IL-1$\beta$ and TNF-$\alpha$ mRNA levels 10-fold less in monocytes cultured in Clq-coated dishes relative to cells cultured in uncoated wells. Similar effects were seen in all other experiments performed with $ClqR_P$ (n=5). This decrease cannot be attributed to a toxic effect on the cells as the mRNA for the ribosomal protein L-32, a housekeeping gene, was present in these cells at levels comparable to those in control cells.

EXAMPLE 9

$ClqR_P$ NEGATIVELY INFLUENCES THE LIPOPOLYSACCHARIDE (LPS) BINDING PROTEIN MEDIATED UPREGULATION OF SPECIFIC CYTOKINES

To determine whether $ClqR_P$ was merely nonstimulatory or, alternatively, if it actively inhibited cytokine synthesis, we compared cytokine mRNA levels in monocytes exposed to LPS and adhered to $ClqR_P$-coated wells to that seen in LPS-treated cells adhered to uncoated control wells. Adherence to $ClqR_P$ resulted in a substantial inhibition of the stimulatory effect of LPS on mRNA levels (n=5) at both 1 h and 18 h of culture for all cytokines detected except for IL-10. The level of IL-1$\alpha$, IL-1$\beta$, TNF-$\alpha$ and IL-6 mRNA in LPS-treated monocytes adhered to $ClqR_P$ at 18 h increased only 2.0-, 3.7-, 1.7- and 2-fold, respectively, in contrast to the 7.5-, 10-, 3- and 6.7-fold higher levels seen in the presence of LPS, all relative to an untreated control. TGF-$\beta$1 mRNA expression was enhanced to a lesser degree (2-fold increase) by LPS. However, even this enhancement was inhibited by adherence of monocytes to $ClqR_P$-coated surfaces. Interestingly, the induction of IL-10 mRNA by LPS at 18 h was not suppressed by $ClqR_P$, but rather was increased by $ClqR_P$ relative to LPS alone.

The inhibitory effects of $ClqR_P$ on cytokine synthesis were observed using several different $ClqR_P$ preparations, suggesting that the inhibition was directly caused by $ClqR_P$ and not by contaminating molecules. Furthermore, the pepsin resistant, collagen-like fragment of $ClqR_P$ which is known to bind to cells and induce enhanced phagocytosis, inhibited cytokine synthesis as well as the intact $ClqR_P$ molecule. Cells incubated under these different conditions were viable and expressed comparable levels of L-32 mRNA.

EXAMPLE 10

$ClqR_P$ NEGATIVELY INFLUENCES THE INCREASE IN IL-1$\alpha$, IL-1$\beta$ AND TNF-$\alpha$ MRNA LEVELS INDUCED BY INTERFERON-$\gamma$ The effect of $ClqR_P$ on another known modulator of monocyte cytokine synthesis, interferon-$\gamma$ (INF-$\gamma$), was assessed to determine if the ability of $ClqR_P$ to suppress LPS-induced cytokine expression was a specific effect on LPS cell signaling or if $ClqR_P$ could modulate cytokine synthesis induced by more than one activator.

At one hour after addition of INF-$\gamma$ (100 U/ml or 300 U/ml), mRNA levels of IL-1$\alpha$, IL-1$\beta$ and TNF-$\alpha$ were increased similar to that following LPS stimulation of monocytes in two of four experiments (in two experiments, cytokine levels were elevated but to a lesser degree than the LPS-treated cells). In all four experiments, adherence to $ClqR_P$ resulted in greatly reduced levels of cytokine mRNA in the INF-$\gamma$-treated cells after only one hour of incubation, suggesting a potential regulatory role for $ClqR_P$ in the induction of these proinflammatory cytokines. Again, induced IL-10 mRNA levels were relatively unchanged by adherence to $ClqR_P$. After 18 h, mRNA levels in the presence of INF-$\gamma$ with or without $ClqR_P$ were unchanged or lower than that of cells in control media.

EXAMPLE 11

$ClqR_P$ INFLUENCES THE SECRETION OF CYTOKINES IL-6, IL-1$\beta$ AND TNF-$\alpha$ The results in Example 10 indicated that $ClqR_P$ contributes to the regulation of mRNA expression of the proinflammatory cytokines, IL-1$\beta$, IL-6 and TNF-$\alpha$. To determine if there was any correlation of mRNA levels with the secretion of IL-6, IL-1$\beta$ and TNF-$\alpha$ under these conditions, the level of these cytokines present in the cell culture media was assessed by ELISA.

Supernatants from monocytes cultured in serum-free media adhered to $ClqR_P$ or SCR1-A or to uncoated wells in the presence or absence of LPS were collected and assayed for IL-1β, TNF-α and IL-6. After 1 h of culture, levels of cytokines in the monocyte supernatants under all conditions were very low (i.e., baseline levels). However, by 18 h of incubation, the concentration of IL-1β and TNF-α in control cultures was elevated over the 1 h time point, and LPS greatly enhanced the concentration of all three cytokine levels. As anticipated from the measured levels of cytokine mRNA after 18 hours, levels of IL-1β (n=6) and TNF-α (n=4) in the media of LPS-treated cells cultured in ClqR$_P$-coated wells were suppressed relative to LPS-stimulated cells in uncoated wells.

Incubation of monocytes for 18 h with SCR1-A also blocked secretion of TNF-α (n=2) and IL-1β (n=3) relative to control cultured monocytes, again consistent with results of RNase protection assay.

EXAMPLE 12

ClqR$_P$ INFLUENCES CYTOKINE MRNA EXPRESSION IN RPMI MEDIUM SUPPLEMENTED WITH 10% FCS

To determine if ClqR$_P$ affects cytokine synthesis in media containing serum, monocytes were cultured in 10% FCS in the presence or absence of ClqR$_P$. Total RNA was isolated and ribonuclease protection assays performed.

After 1 h of culture, levels of TGF-β1, IL-1β and TNF-α mRNA were nearly identical in the control and Clq-adherent monocytes. Similarly, after 18 hours in culture, levels of mRNA for the cytokines assayed were barely detectable in either the control cells or cells adhered to ClqR$_P$. Cells incubated under these different conditions showed distinct morphology by microscopic observation, but all were viable. Thus, in both serum-free defined media and serum-containing media, ClqR$_P$ does not activate the monocyte/macrophage to produced these proinflammatory cytokines.

EXAMPLE 13

ClqR$_P$ EFFECT ON LPS UPREGULATION OF CYTOKINE EXPRESSION

Fetal calf serum is known to contain LBP, a LPS binding protein, which results in an increased functional response to LPS in cells expressing CD14. We therefore investigated whether ClqR$_P$ was able to modulate the LPS-mediated upregulation of cytokine expression when cells were cultured in serum-containing media.

Monocytes incubated with LPS demonstrated a robust stimulation of all cytokine MRNA levels (except TNF-β and GM-CSF), which was either not inhibited by the adherence of cells to Clq-coated surfaces at either 1 h or 18 h of culture or only minimally inhibited. Thus, the data suggest that in serum-containing media, LPS triggers a dominant stimulating effect on cytokine gene expression in monocytes which is not altered by ClqR$_P$. Stimulation of these mRNA levels by LPS was also not inhibited by SCR1-A, HSA or fibronectin at 1 h or 18 h of culture in the presence of serum (n=2).

Finally, the effect of ClqR$_P$ on the levels of IL-6, IL-1β and TNF-α in culture supernatants of monocytes in serum-containing media were assayed. Cytokine levels of cells adherent to ClqR$_P$ were found to be near baseline levels in control cultures at 1 h and did not increase after 18 h of culture. In LPS-stimulated cells, after one hour of incubation, the level of TNF-α, but not IL-1β, was increased in cell supernatants, even though LPS triggered enhanced levels of mRNA for both cytokines at the early time point. After 18 h, as expected, LPS treatment significantly increased IL-6, IL-1β and TNF-α levels relative to the unstimulated control samples. ClqR$_P$ did not have any inhibitory effect on LPS-induced secretion of these cytokines in monocytes cultured in serum-containing media, consistent with its minimal modulation of the LPS-induced mRNA levels of these cytokines in cells in serum.

A number of embodiments of the present invention have been described. Nevertheless, it will be understood that various modifications may be made without departing from the spirit and scope of the invention. Accordingly, it is to be understood that the invention is not to be limited by the specific illustrated embodiment, but only by the scope of the appended claims.

---

What is claimed is:

1. An isolated nucleic acid molecule encoding an amino acid sequence as set forth in SEQ ID NO:2.

2. An isolated nucleic acid molecule having a nucleotide sequence as set forth in SEQ ID NO:1.

3. An isolated nucleic acid molecule that hybridizes to a nucleic acid of claim 1 or 2 and encodes a ClqR$_P$ protein.

4. An isolated nucleic acid molecule of claim 1 or 2, wherein the nucleic acid is from a mammal.

5. An isolated nucleic acid molecule of claim 1 or 2, wherein the nucleic acid is from a human.

6. An expression vector containing the nucleic acid of claim 1.

7. An isolated cell containing the vector of claim 6.

8. An isolated nucleic acid molecule selected from the group consisting of:

a) the nucleotide sequence of SEQ ID NO: 1, where T can also be U;

b) a nucleic acid sequence that hybridizes to the nucleotide sequence of SEQ ID NO: 1 or to the complement of the nucleotide sequence of SEQ ID NO: 1, and encodes a ClqR$_P$ protein;

c) a fragment of a) that comprises 15 nucleotides; and d) SEQ ID NO:1.

9. A method for delivery and expression of ClqR$_P$ in a target cell, wherein the method comprises:

a) delivering a nucleic acid encoding ClqR$_P$ into a target cell, in vitro; and b) expressing said nucleic acid inside the target cell.

10. The method of claim 9, further comprising detecting the level of ClqR$_P$ mRNA in the target cell subsequent to step b).

\* \* \* \* \*

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
      (A) LENGTH: 3460 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 149..2105

(xi) SEQUENCE DESCRIPTION: SEQ ID NO:1:

AAAGCCCTCA GCCTTTGTGT CCTTCTCTGC GCCGGAGTGG CTGCAGCTCA CCCCTCAGCT    60

```
CCCCTTGGGG CCCAGCTGGG AGCCGAGATA GAAGCTCCTG TCGCCGCTGG GCTTCTCGCC          120

TCCCGCAGAG GGCCACACAG AGACCGGG ATG GCC ACC TCC ATG GGC CTG CTG            172
                                Met Ala Thr Ser Met Gly Leu Leu
                                 1               5

CTG CTG CTG CTG CTG CTC CTG ACC CAG CCC GGG GCG GGG ACG GGA GCT           220
Leu Leu Leu Leu Leu Leu Leu Thr Gln Pro Gly Ala Gly Thr Gly Ala
        10                  15                  20

GAC ACG GAG GCG GTG GTC TGC GTG GGG ACC GCC TGC TAC ACG GCC CAC           268
Asp Thr Glu Ala Val Val Cys Val Gly Thr Ala Cys Tyr Thr Ala His
 25              30                  35                      40

TCG GGC AAG CTG AGC GCT GCC GAG GCC CAG AAC CAC TGC AAC CAG AAC           316
Ser Gly Lys Leu Ser Ala Ala Glu Ala Gln Asn His Cys Asn Gln Asn
                    45                  50                  55

GGG GGC AAC CTG GCC ACT GTG AAG AGC AAG GAG GAG GCC CAG CAC GTC           364
Gly Gly Asn Leu Ala Thr Val Lys Ser Lys Glu Glu Ala Gln His Val
                60                  65                  70

CAG CGA GTA CTG GCC CAG CTC CTG AGG CGG GAG GCA GCC CTG ACG GCG           412
Gln Arg Val Leu Ala Gln Leu Leu Arg Arg Glu Ala Ala Leu Thr Ala
            75                  80                  85

AGG ATG AGC AAG TTC TGG ATT GGG CTC CAG CGA GAG AAG GGC AAG TGC           460
Arg Met Ser Lys Phe Trp Ile Gly Leu Gln Arg Glu Lys Gly Lys Cys
        90                  95                 100

CTG GAC CCT AGT CTG CCG CTG AAG GGC TTC AGC TGG GTG GGC GGG GGG           508
Leu Asp Pro Ser Leu Pro Leu Lys Gly Phe Ser Trp Val Gly Gly Gly
105                 110                 115                 120

GAG GAC ACG CCT TAC TCT AAC TGG CAC AAG GAG CTC CGG AAC TCG TGC           556
Glu Asp Thr Pro Tyr Ser Asn Trp His Lys Glu Leu Arg Asn Ser Cys
                125                 130                 135

ATC TCC AAG CGC TGT GTG TCT CTG CTG CTG GAC CTG TCC CAG CCG CTC           604
Ile Ser Lys Arg Cys Val Ser Leu Leu Leu Asp Leu Ser Gln Pro Leu
            140                 145                 150

CTT CCC AAC CGC CTG CCC AAG TGG TCT GAG GGC CCC TGT GGG AGC CCA           652
Leu Pro Asn Arg Leu Pro Lys Trp Ser Glu Gly Pro Cys Gly Ser Pro
        155                 160                 165

GGC TCC CCC GGA AGT AAC ATT GAG GGC TTC GTG TGC AAG TTC AGC TTC           700
Gly Ser Pro Gly Ser Asn Ile Glu Gly Phe Val Cys Lys Phe Ser Phe
170                 175                 180

AAA GGC ATG TGC CGG CCT CTG GCC CTG GGG GGC CCA GGT CAG GTG ACC           748
Lys Gly Met Cys Arg Pro Leu Ala Leu Gly Gly Pro Gly Gln Val Thr
185                 190                 195                 200

TAC ACC ACC CCC TTC CAG ACC ACC AGT TCC TCC TTG GAG GCT GTG CCC           796
Tyr Thr Thr Pro Phe Gln Thr Thr Ser Ser Ser Leu Glu Ala Val Pro
                205                 210                 215

TTT GCC TCT GCG GCC AAT GTA GCC TGT GGG GAA GGT GAC AAG GAC GAG           844
Phe Ala Ser Ala Ala Asn Val Ala Cys Gly Glu Gly Asp Lys Asp Glu
            220                 225                 230

ACT CAG AGT CAT TAT TTC CTG TGC AAG GAG AAG GCC CCC GAT GTG TTC           892
Thr Gln Ser His Tyr Phe Leu Cys Lys Glu Lys Ala Pro Asp Val Phe
        235                 240                 245

GAC TGG GGC AGC TCG GGC CCC CTC TGT GTC AGC CCC AAG TAT GGC TGC           940
Asp Trp Gly Ser Ser Gly Pro Leu Cys Val Ser Pro Lys Tyr Gly Cys
250                 255                 260

AAC TTC AAC AAT GGG GGC TGC CAC CAG GAC TGC TTT GAA GGG GGG GAT           988
Asn Phe Asn Asn Gly Gly Cys His Gln Asp Cys Phe Glu Gly Gly Asp
265                 270                 275                 280

GGC TCC TTC CTC TGC GGC TGC CGA CCA GGA TTC CGG CTG CTG GAT GAC           1036
Gly Ser Phe Leu Cys Gly Cys Arg Pro Gly Phe Arg Leu Leu Asp Asp
                285                 290                 295

CTG GTG ACC TGT GCC TCT CGA AAC CCT TGC AGC TCC AGC CCA TGT CGT           1084
Leu Val Thr Cys Ala Ser Arg Asn Pro Cys Ser Ser Ser Pro Cys Arg
```

-continued

|  |  |  |  |  |  |  |  |  |  |  |  |  |  |  |  |
|---|---|---|---|---|---|---|---|---|---|---|---|---|---|---|---|
|  |  | 300 |  |  |  | 305 |  |  |  | 310 |  |  |  |  |  |
| GGG | GGG | GCC | ACG | TGC | GTC | CTG | GGA | CCC | CAT | GGG | AAA | AAC | TAC | ACG | TGC | 1132 |
| Gly | Gly | Ala | Thr | Cys | Val | Leu | Gly | Pro | His | Gly | Lys | Asn | Tyr | Thr | Cys |
|  |  | 315 |  |  |  | 320 |  |  |  | 325 |  |  |  |  |  |
| CGC | TGC | CCC | CAA | GGG | TAC | CAG | CTG | GAC | TCG | AGT | CAG | CTG | GAC | TGT | GTG | 1180 |
| Arg | Cys | Pro | Gln | Gly | Tyr | Gln | Leu | Asp | Ser | Ser | Gln | Leu | Asp | Cys | Val |
|  |  | 330 |  |  |  | 335 |  |  |  | 340 |  |  |  |  |  |
| GAC | GTG | GAT | GAA | TGC | CAG | GAC | TCC | CCC | TGT | GCC | CAG | GAG | TGT | GTC | AAC | 1228 |
| Asp | Val | Asp | Glu | Cys | Gln | Asp | Ser | Pro | Cys | Ala | Gln | Glu | Cys | Val | Asn |
| 345 |  |  |  | 350 |  |  |  | 355 |  |  |  | 360 |  |  |  |
| ACC | CCT | GGG | GGC | TTC | CGC | TGC | GAA | TGC | TGG | GTT | GGC | TAT | GAG | CCG | GGC | 1276 |
| Thr | Pro | Gly | Gly | Phe | Arg | Cys | Glu | Cys | Trp | Val | Gly | Tyr | Glu | Pro | Gly |
|  |  |  | 365 |  |  |  | 370 |  |  |  | 375 |  |  |  |  |
| GGT | CCT | GGA | GAG | GGG | GCC | TGT | CAG | GAT | GTG | GAT | GAG | TGT | GCT | CTG | GGT | 1324 |
| Gly | Pro | Gly | Glu | Gly | Ala | Cys | Gln | Asp | Val | Asp | Glu | Cys | Ala | Leu | Gly |
|  |  |  | 380 |  |  |  | 385 |  |  |  | 390 |  |  |  |  |
| CGC | TCG | CCT | TGC | GCC | CAG | GGC | TGC | ACC | AAC | ACA | GAT | GGC | TCA | TTT | CAC | 1372 |
| Arg | Ser | Pro | Cys | Ala | Gln | Gly | Cys | Thr | Asn | Thr | Asp | Gly | Ser | Phe | His |
|  |  | 395 |  |  |  | 400 |  |  |  | 405 |  |  |  |  |  |
| TGC | TCC | TGT | GAG | GAG | GGC | TAC | GTC | CTG | GCC | GGG | GAG | GAC | GGG | ACT | CAG | 1420 |
| Cys | Ser | Cys | Glu | Glu | Gly | Tyr | Val | Leu | Ala | Gly | Glu | Asp | Gly | Thr | Gln |
|  | 410 |  |  |  | 415 |  |  |  | 420 |  |  |  |  |  |  |
| TGC | CAG | GAC | GTG | GAT | GAG | TGT | GTG | GGC | CCG | GGG | GCC | CCC | CTC | TGC | GAC | 1468 |
| Cys | Gln | Asp | Val | Asp | Glu | Cys | Val | Gly | Pro | Gly | Gly | Pro | Leu | Cys | Asp |
| 425 |  |  |  | 430 |  |  |  | 435 |  |  |  | 440 |  |  |  |
| AGC | TTG | TGC | TTC | AAC | ACA | CAA | GGG | TCC | TTC | CAC | TGT | GGC | TGC | CTG | CCA | 1516 |
| Ser | Leu | Cys | Phe | Asn | Thr | Gln | Gly | Ser | Phe | His | Cys | Gly | Cys | Leu | Pro |
|  |  |  | 445 |  |  |  | 450 |  |  |  | 455 |  |  |  |  |
| GGC | TGG | GTG | CTG | GCC | CCA | AAT | GGG | GTC | TCT | TGC | ACC | ATG | GGG | CCT | GTG | 1564 |
| Gly | Trp | Val | Leu | Ala | Pro | Asn | Gly | Val | Ser | Cys | Thr | Met | Gly | Pro | Val |
|  |  | 460 |  |  |  | 465 |  |  |  | 470 |  |  |  |  |  |
| TCT | CTG | GGA | CCA | CCA | TCT | GGG | CCC | CCC | GAT | GAG | GAG | GAC | AAA | GGA | GAG | 1612 |
| Ser | Leu | Gly | Pro | Pro | Ser | Gly | Pro | Pro | Asp | Glu | Glu | Asp | Lys | Gly | Glu |
|  |  | 475 |  |  |  | 480 |  |  |  | 485 |  |  |  |  |  |
| AAA | GAA | GGG | AGC | ACC | GTG | CCC | CGC | GCT | GCA | ACA | GCC | AGT | CCC | ACA | AGG | 1660 |
| Lys | Glu | Gly | Ser | Thr | Val | Pro | Arg | Ala | Ala | Thr | Ala | Ser | Pro | Thr | Arg |
|  | 490 |  |  |  | 495 |  |  |  | 500 |  |  |  |  |  |  |
| GGC | CCC | GAG | GGC | ACC | CCC | AAG | GCT | ACA | CCC | ACC | ACA | AGT | AGA | CCT | TCG | 1708 |
| Gly | Pro | Glu | Gly | Thr | Pro | Lys | Ala | Thr | Pro | Thr | Thr | Ser | Arg | Pro | Ser |
| 505 |  |  |  | 510 |  |  |  | 515 |  |  |  | 520 |  |  |  |
| CTG | TCA | TCT | GAC | GCC | CCC | ATC | ACA | TCT | GCC | CCA | CTC | AAG | ATG | CTG | GCC | 1756 |
| Leu | Ser | Ser | Asp | Ala | Pro | Ile | Thr | Ser | Ala | Pro | Leu | Lys | Met | Leu | Ala |
|  |  |  | 525 |  |  |  | 530 |  |  |  | 535 |  |  |  |  |
| CCC | AGT | GGG | TCC | TCA | GGC | GTC | TGG | AGG | GAG | CCC | AGC | ATC | CAT | CAC | GCC | 1804 |
| Pro | Ser | Gly | Ser | Ser | Gly | Val | Trp | Arg | Glu | Pro | Ser | Ile | His | His | Ala |
|  |  | 540 |  |  |  | 545 |  |  |  | 550 |  |  |  |  |  |
| ACA | GCT | GCC | TCT | GGC | CCC | CAG | GAG | CCT | GCA | GGT | GGG | GAC | TCC | TCC | GTG | 1852 |
| Thr | Ala | Ala | Ser | Gly | Pro | Gln | Glu | Pro | Ala | Gly | Gly | Asp | Ser | Ser | Val |
|  |  | 555 |  |  |  | 560 |  |  |  | 565 |  |  |  |  |  |
| GCC | ACA | CAA | AAC | AAC | GAT | GGC | ACT | GAC | GGG | CAA | AAG | CTG | CTT | TTA | TTC | 1900 |
| Ala | Thr | Gln | Asn | Asn | Asp | Gly | Thr | Asp | Gly | Gln | Lys | Leu | Leu | Leu | Phe |
|  | 570 |  |  |  | 575 |  |  |  | 580 |  |  |  |  |  |  |
| TAC | ATC | CTA | GGC | ACC | GTG | GTG | GCC | ATC | CTA | CTC | CTG | CTG | GCC | CTG | GCT | 1948 |
| Tyr | Ile | Leu | Gly | Thr | Val | Val | Ala | Ile | Leu | Leu | Leu | Leu | Ala | Leu | Ala |
| 585 |  |  |  | 590 |  |  |  | 595 |  |  |  | 600 |  |  |  |
| CTG | GGG | CTA | CTG | GTC | TAT | CGC | AAG | CGG | AGA | GCG | AAG | AGG | GAG | GAG | AAG | 1996 |
| Leu | Gly | Leu | Leu | Val | Tyr | Arg | Lys | Arg | Arg | Ala | Lys | Arg | Glu | Glu | Lys |
|  |  |  | 605 |  |  |  | 610 |  |  |  | 615 |  |  |  |  |
| AAG | GAG | AAG | AAG | CCC | CAG | AAT | GCG | GCA | GAC | AGT | TAC | TCC | TGG | GTT | CCA | 2044 |
| Lys | Glu | Lys | Lys | Pro | Gln | Asn | Ala | Ala | Asp | Ser | Tyr | Ser | Trp | Val | Pro |

```
              620             625             630
GAG CGA GCT GAG AGC AGG GCC ATG GAG AAC CAG TAC AGT CCG ACA CCT    2092
Glu Arg Ala Glu Ser Arg Ala Met Glu Asn Gln Tyr Ser Pro Thr Pro
            635             640             645

GGG ACA GAC TGC T GAAAGTGAGG TGGCCCTAGA GACACTAGAG TCACCAGCCA      2145
Gly Thr Asp Cys
    650

CCATCCTCAG AGCTTTGAAC TCCCCATTCC AAAGGGCAC CCACATTTTT TTGAAAGACT   2205

GGACTGGAAT CTTAGCAAAC AATTGTAAGT CTCCTCCTTA AAGGCCCCTT GGAACATGCA  2265

GGTATTTTCT ACGGGTGTTT GATGTTCCTG AAGTGGAAGC TGTGTGTTGG CGTGCCACGG  2325

TGGGGATTTC GTGACTCTAT AATGATTGTT ACTCCCCCTC CCTTTTCAAA TTCCAATGTG  2385

ACCAATTCCG GATCAGGGTG TGAGGAGGCT GGGGCTAAGG GGCTCCCCTG AATATCTTCT  2445

CTGCTCACTT CCACCATCTA AGAGGAAAAG GTGAGTTGCT CATGCTGATT AGGATTGAAA  2505

TGATTTGTTT CTCTTCCTAG GATGAAAACT AAATCAATTA ATTATTCAAT TAGGTAAGAA  2565

GATCTGGTTT TTTGGTCAAA GGGAACATGT TCGGACTGGA AACATTTCTT TACATTTGCA  2625

TTCCTCCATT TCGCCAGCAC AAGTCTTGCT AAATGTGATA CTGTTGACAT CCTCCAGAAT  2685

GGCCAGAAGT GCAATTAACC TCTTAGGTGG CAAGGAGGCA GGAAGTGCCT CTTTAGTTCT  2745

TACATTTCTA ATAGCCTTGG GTTTATTTGC AAAGGAAGCT TGAAAAATAT GAGAAAAGTT  2805

GCTTGAAGTG CATTACAGGT GTTTGTGAAG TCACATAATC TACGGGGCTA GGGCGAGAGA  2865

GGCCAGGGAT TTGTTCACAG ATACTTGAAT TAATTCATCC AAATGTACTG AGGTTACCAC  2925

ACACTTGACT ACGGATGTGA TCAACACTAA CAAGGAAACA AATTCAAGGA CAACCTGTCT  2985

TTGAGCCAGG GCAGGCCTCA GACACCCTGC CTGTGGCCCC GCCTCCACTT CATCCTGCCC  3045

GGAATGCCAG TGCTCCGAGC TCAGACAGAG GAAGCCCTGC AGAAAGTTCC ATCAGGCTGT  3105

TTCCTAAAGG ATGTGTGAAC GGGAGATGAT GCACTGTGTT TTGAAAGTTG TCATTTTAAA  3165

GCATTTTAGC ACAGTTCATA GTCCACAGTT GATGCAGCAT CCTGAGATTT TAAATCCTGA  3225

AGTGTGGGTG GCGCACACAC CAAGTAGGGA GCTAGTCAGG CAGTTTGCTT AAGGAACTTT  3285

TGTTCTCTGT CTCTTTTCCT TAAAATTGGG GGTAAGGAGG GAAGGAAGAG GGAAAGAGAT  3345

GACTAACTAA AATCATTTTT ACAGCAAAAA CTGCTCAAAG CCATTTAAAT TATATCCTCA  3405

TTTTAAAAGT TACATTTGCA AATATTTCTC CCTATGATAA TGCAGTCGAT AGTGT        3460

(2) INFORMATION FOR SEQ ID NO:2:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Thr Ser Met Gly Leu Leu Leu Leu Leu Leu Leu Leu Leu Thr
 1               5                  10                  15

Gln Pro Gly Ala Gly Thr Gly Ala Asp Thr Glu Ala Val Val Cys Val
                20                  25                  30

Gly Thr Ala Cys Tyr Thr Ala His Ser Gly Lys Leu Ser Ala Ala Glu
        35                  40                  45

Ala Gln Asn His Cys Asn Gln Asn Gly Gly Asn Leu Ala Thr Val Lys
    50                  55                  60

Ser Lys Glu Glu Ala Gln His Val Gln Arg Val Leu Ala Gln Leu Leu
65                  70                  75                  80
```

```
Arg Arg Glu Ala Ala Leu Thr Ala Arg Met Ser Lys Phe Trp Ile Gly
             85                  90                  95

Leu Gln Arg Glu Lys Gly Lys Cys Leu Asp Pro Ser Leu Pro Leu Lys
            100                 105                 110

Gly Phe Ser Trp Val Gly Gly Glu Asp Thr Pro Tyr Ser Asn Trp
        115                 120                 125

His Lys Glu Leu Arg Asn Ser Cys Ile Ser Lys Arg Cys Val Ser Leu
    130                 135                 140

Leu Leu Asp Leu Ser Gln Pro Leu Leu Pro Asn Arg Leu Pro Lys Trp
145                 150                 155                 160

Ser Glu Gly Pro Cys Gly Ser Pro Gly Ser Pro Gly Ser Asn Ile Glu
                165                 170                 175

Gly Phe Val Cys Lys Phe Ser Phe Lys Gly Met Cys Arg Pro Leu Ala
            180                 185                 190

Leu Gly Gly Pro Gly Gln Val Thr Tyr Thr Thr Pro Phe Gln Thr Thr
        195                 200                 205

Ser Ser Ser Leu Glu Ala Val Pro Phe Ala Ser Ala Ala Asn Val Ala
    210                 215                 220

Cys Gly Glu Gly Asp Lys Asp Glu Thr Gln Ser His Tyr Phe Leu Cys
225                 230                 235                 240

Lys Glu Lys Ala Pro Asp Val Phe Asp Trp Gly Ser Ser Gly Pro Leu
                245                 250                 255

Cys Val Ser Pro Lys Tyr Gly Cys Asn Phe Asn Asn Gly Gly Cys His
            260                 265                 270

Gln Asp Cys Phe Glu Gly Gly Asp Gly Ser Phe Leu Cys Gly Cys Arg
        275                 280                 285

Pro Gly Phe Arg Leu Leu Asp Asp Leu Val Thr Cys Ala Ser Arg Asn
290                 295                 300

Pro Cys Ser Ser Ser Pro Cys Arg Gly Gly Ala Thr Cys Val Leu Gly
305                 310                 315                 320

Pro His Gly Lys Asn Tyr Thr Cys Arg Cys Pro Gln Gly Tyr Gln Leu
                325                 330                 335

Asp Ser Ser Gln Leu Asp Cys Val Asp Val Asp Glu Cys Gln Asp Ser
            340                 345                 350

Pro Cys Ala Gln Glu Cys Val Asn Thr Pro Gly Gly Phe Arg Cys Glu
        355                 360                 365

Cys Trp Val Gly Tyr Glu Pro Gly Gly Pro Gly Glu Gly Ala Cys Gln
370                 375                 380

Asp Val Asp Glu Cys Ala Leu Gly Arg Ser Pro Cys Ala Gln Gly Cys
385                 390                 395                 400

Thr Asn Thr Asp Gly Ser Phe His Cys Ser Cys Glu Glu Gly Tyr Val
                405                 410                 415

Leu Ala Gly Glu Asp Gly Thr Gln Cys Gln Asp Val Asp Glu Cys Val
            420                 425                 430

Gly Pro Gly Gly Pro Leu Cys Asp Ser Leu Cys Phe Asn Thr Gln Gly
        435                 440                 445

Ser Phe His Cys Gly Cys Leu Pro Gly Trp Val Leu Ala Pro Asn Gly
    450                 455                 460

Val Ser Cys Thr Met Gly Pro Val Ser Leu Gly Pro Pro Ser Gly Pro
465                 470                 475                 480

Pro Asp Glu Glu Asp Lys Gly Glu Lys Glu Gly Ser Thr Val Pro Arg
                485                 490                 495

Ala Ala Thr Ala Ser Pro Thr Arg Gly Pro Glu Gly Thr Pro Lys Ala
```

```
                    500                 505                 510
Thr Pro Thr Thr Ser Arg Pro Ser Leu Ser Ser Asp Ala Pro Ile Thr
            515                 520                 525

Ser Ala Pro Leu Lys Met Leu Ala Pro Ser Gly Ser Ser Gly Val Trp
530                 535                 540

Arg Glu Pro Ser Ile His His Ala Thr Ala Ala Ser Gly Pro Gln Glu
545                 550                 555                 560

Pro Ala Gly Gly Asp Ser Ser Val Ala Thr Gln Asn Asn Asp Gly Thr
                565                 570                 575

Asp Gly Gln Lys Leu Leu Leu Phe Tyr Ile Leu Gly Thr Val Val Ala
            580                 585                 590

Ile Leu Leu Leu Leu Ala Leu Ala Leu Gly Leu Leu Val Tyr Arg Lys
        595                 600                 605

Arg Arg Ala Lys Arg Glu Glu Lys Lys Glu Lys Lys Pro Gln Asn Ala
610                 615                 620

Ala Asp Ser Tyr Ser Trp Val Pro Glu Arg Ala Glu Ser Arg Ala Met
625                 630                 635                 640

Glu Asn Gln Tyr Ser Pro Thr Pro Gly Thr Asp Cys
                645                 650
```

(2) INFORMATION FOR SEQ ID NO:3:

(i) SEQUENCE CHARACTERISTICS:
        (A) LENGTH: 42 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:3:

```
Pro Lys Tyr Gly Cys Asn Phe Asn Asn Gly Gly Cys His Gln Asp Cys
1               5                   10                  15

Phe Glu Gly Gly Asp Gly Ser Phe Leu Cys Gly Cys Arg Pro Gly Phe
                20                  25                  30

Arg Leu Leu Asp Asp Leu Val Thr Cys Ala
            35                  40
```

(2) INFORMATION FOR SEQ ID NO:4:

(i) SEQUENCE CHARACTERISTICS:
        (A) LENGTH: 43 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:4:

```
Ser Arg Asn Pro Cys Ser Ser Pro Cys Arg Gly Gly Ala Thr Cys
1               5                   10                  15

Val Leu Gly Pro His Gly Lys Asn Tyr Thr Cys Arg Cys Pro Gln Gly
                20                  25                  30

Tyr Gln Leu Asp Ser Ser Gln Leu Asp Cys Val
            35                  40
```

(2) INFORMATION FOR SEQ ID NO:5:

(i) SEQUENCE CHARACTERISTICS:
        (A) LENGTH: 40 amino acids
        (B) TYPE: amino acid
        (C) STRANDEDNESS: Not Relevant (D) TOPOLOGY: linear (ii) MOLECULE TYPE: peptide (xi) SEQUENCE DESCRIPTION: SEQ ID NO:5:

Asp Val Asp Glu Cys Gln Asp Ser Pro Cys Ala Gln Glu Cys Val Asn
1               5                   10                  15

Thr Pro Gly Gly Phe Arg Cys Glu Cys Trp Val Gly Tyr Glu Pro Gly
            20                  25                  30

Gly Pro Gly Glu Gly Ala Cys Gln
        35                  40

(2) INFORMATION FOR SEQ ID NO:6:

(i) SEQUENCE CHARACTERISTICS:
           (A) LENGTH: 34 amino acids
           (B) TYPE: amino acid
           (C) STRANDEDNESS: Not Relevant
           (D) TOPOLOGY: linear (ii) MOLECULE TYPE: peptide (xi) SEQUENCE DESCRIPTION: SEQ ID NO:6:

Gly Gly Pro Gly Gln Val Thr Tyr Thr Thr Pro Phe Gln Thr Thr Ser
1               5                   10                  15

Ser Ser Leu Glu Ala Val Pro Phe Ala Ser Ala Ala Asn Val Ala Cys
            20                  25                  30

Gly Glu (2) INFORMATION FOR SEQ ID NO:7:

(i) SEQUENCE CHARACTERISTICS:
           (A) LENGTH: 42 amino acids
           (B) TYPE: amino acid
           (C) STRANDEDNESS: Not Relevant
           (D) TOPOLOGY: linear (ii) MOLECULE TYPE: peptide (xi) SEQUENCE DESCRIPTION: SEQ ID NO:7:

Asp Val Asp Glu Cys Ala Leu Gly Arg Ser Pro Cys Ala Gln Gly Cys
1               5                   10                  15

Thr Asn Thr Asp Gly Ser Phe His Cys Ser Cys Glu Glu Gly Tyr Val
            20                  25                  30

Leu Ala Gly Glu Asp Gly Thr Gln Cys Gln
        35                  40

(2) INFORMATION FOR SEQ ID NO:8:

(i) SEQUENCE CHARACTERISTICS:
           (A) LENGTH: 25 amino acids
           (B) TYPE: amino acid
           (C) STRANDEDNESS: Not Relevant
           (D) TOPOLOGY: linear (ii) MOLECULE TYPE: peptide (xi) SEQUENCE DESCRIPTION: SEQ ID NO:8:

Leu Leu Leu Phe Tyr Ile Leu Gly Thr Val Val Ala Ile Leu Leu Leu
1               5                   10                  15

Leu Ala Leu Ala Leu Gly Leu Leu Val
            20                  25

(2) INFORMATION FOR SEQ ID NO:9:

(i) SEQUENCE CHARACTERISTICS:
            (A) LENGTH: 42 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:9:

Asp Val Asp Glu Cys Val Gly Pro Gly Gly Pro Leu Cys Asp Ser Leu
1               5                   10                  15

Cys Phe Asn Thr Gln Gly Ser Phe His Cys Gly Cys Leu Pro Gly Trp
            20                  25                  30

Val Leu Ala Pro Asn Gly Val Ser Cys Thr
        35                  40

(2) INFORMATION FOR SEQ ID NO:10:

(i) SEQUENCE CHARACTERISTICS:
            (A) LENGTH: 47 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:10:

Tyr Arg Lys Arg Arg Ala Lys Arg Glu Glu Lys Lys Glu Lys Lys Pro
1               5                   10                  15

Gln Asn Ala Ala Asp Ser Tyr Ser Trp Val Pro Glu Arg Ala Glu Ser
            20                  25                  30

Arg Ala Met Glu Asn Gln Tyr Ser Pro Thr Pro Gly Thr Asp Cys
        35                  40                  45

(2) INFORMATION FOR SEQ ID NO:11:

(i) SEQUENCE CHARACTERISTICS:
            (A) LENGTH: 11 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:11:

Val Gly Gly Gly Glu Asp Thr Pro Tyr Ser Asn
1               5                   10

(2) INFORMATION FOR SEQ ID NO:12:

(i) SEQUENCE CHARACTERISTICS:
            (A) LENGTH: 12 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:12:

Val Gly Gly Gly Glu Asp Thr Pro Tyr Ser Asn Lys
1               5                   10

(2) INFORMATION FOR SEQ ID NO:13:

(i) SEQUENCE CHARACTERISTICS:
            (A) LENGTH: 9 amino acids
            (B) TYPE: amino acid
            (C) STRANDEDNESS: Not Relevant -continued (D) TOPOLOGY: linear (ii) MOLECULE TYPE: peptide (xi) SEQUENCE DESCRIPTION: SEQ ID NO:13:

```
Phe Trp Ile Gly Leu Gln Arg Glu Lys
1               5
```

(2) INFORMATION FOR SEQ ID NO:14:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:14:

```
Gly Phe Ser Xaa Val Gly Gly Glu Asp Thr Pro Tyr Ser Asn Xaa
1               5                   10                  15
His Lys
```

(2) INFORMATION FOR SEQ ID NO:15:

(i) SEQUENCE CHARACTERISTICS:
        (A) LENGTH: 22 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:15:

```
Val Gly Ala Asp Thr Glu Ala Val Val Xaa Xaa Gly Thr Ala Thr Tyr
1               5                   10                  15
Arg Ile His Xaa Lys Leu
            20
```

(2) INFORMATION FOR SEQ ID NO:16:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:16:

```
Xaa Gly Ala Thr Val Pro Gln Ala Ala Thr Ala Ser Pro Thr Gly Gly
1               5                   10                  15
Pro Glu Gly Val
            20
```

(2) INFORMATION FOR SEQ ID NO:17:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:17:

```
Ala Thr Pro Thr Thr Ser Arg Pro Ser Leu
1               5                   10
```

(2) INFORMATION FOR SEQ ID NO:18:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:18:

```
Gly Phe Ser Trp Val Gly Gly Gly Glu Asp Thr Pro Xaa Asn Xaa His
1               5                   10                  15

Lys
```

(2) INFORMATION FOR SEQ ID NO:19:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:19:

```
Ala Pro Asp Val Phe Asp Trp Gly Ser Xaa Gly Pro Leu Xaa Val Tyr
1               5                   10                  15
```

(2) INFORMATION FOR SEQ ID NO:20:

(i) SEQUENCE CHARACTERISTICS:
        (A) LENGTH: 23 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:20:

```
Ala Met Xaa Xaa Pro Leu Ala Leu Gly Gly Pro Gly Gln Val Thr Tyr
1               5                   10                  15

Thr Thr Pro Phe Gln Xaa Thr
                20
```

(2) INFORMATION FOR SEQ ID NO:21:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:21:

```
Lys Pro Gln Asn Ala Ala Asp Ser Tyr Ser Trp Val Pro Glu Arg
1               5                   10                  15
```

(2) INFORMATION FOR SEQ ID NO:22:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:22:

Val Leu Ala Gln Leu Leu Arg
1               5

(2) INFORMATION FOR SEQ ID NO:23:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:23:

Phe Trp Ile Gly Leu Gln Arg
1               5

(2) INFORMATION FOR SEQ ID NO:24:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:24:

Gly Phe Ser Trp Val Gly Gly Gly Glu Asp Thr Pro Tyr Ser Asn Trp
1               5                   10                  15

His Lys (2) INFORMATION FOR SEQ ID NO:25:

(i) SEQUENCE CHARACTERISTICS:
        (A) LENGTH: 27 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:25:

Thr Thr Pro Phe Gln Thr Thr Ser Ser Ser Leu Glu Ala Val Pro Phe
1               5                   10                  15

Ala Ser Ala Ala Asn Val Ala Ala Gly Glu Gly
            20                  25

(2) INFORMATION FOR SEQ ID NO:26:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:26:

Tyr Gly Xaa Asn Phe Xaa Asn Gly
1               5

(2) INFORMATION FOR SEQ ID NO:27:

(i) SEQUENCE CHARACTERISTICS:
        (A) LENGTH: 10 amino acids (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:27:

Pro Gln Gly Tyr Gln Leu Asp Xaa Xaa Gln
1               5                   10

(2) INFORMATION FOR SEQ ID NO:28:

(i) SEQUENCE CHARACTERISTICS:
            (A) LENGTH: 4 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:28:

Met Leu Ala Pro
1

(2) INFORMATION FOR SEQ ID NO:29:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:29:

TTGGCCGCAG AGGCAAAGGG CA                                              22

(2) INFORMATION FOR SEQ ID NO:30:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:30:

CAAGGAGGAA CTGGTGGTCT GG                                              22

(2) INFORMATION FOR SEQ ID NO:31:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:31:

TGGGCCTCGG CAGCGCTCAG CT                                              22

(2) INFORMATION FOR SEQ ID NO:32:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:32:

GGAGCTGGAG CTCCAGCTGG AGCTCAAGGT AGCTAC                               36

(2) INFORMATION FOR SEQ ID NO:33:

(i) SEQUENCE CHARACTERISTICS:
        (A) LENGTH: 19 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:33:

```
Gly Gly Ile Gly Cys Ile Gly Ala Thr Cys Ala Cys Ile Gly Ala Ala
1               5                   10                  15
Gly Gly Cys
```